(12) United States Patent
Johnson

(10) Patent No.: US 6,190,923 B1
(45) Date of Patent: Feb. 20, 2001

(54) DIETHYLENETRIAMINE-N,N',N"-TRIACETIC ACID DERIVATIVES

(76) Inventor: David K. Johnson, 923 S. Fourth St., Silver Lake, WI (US) 53170

(*) Notice: Under 35 U.S.C. 154(b), the term of this patent shall be extended for 0 days.

(21) Appl. No.: 09/148,733

(22) Filed: Sep. 4, 1998

Related U.S. Application Data

(60) Provisional application No. 60/058,114, filed on Sep. 5, 1997.

(51) Int. Cl.$^7$ ................. G01N 33/533; C07D 417/12; C07D 413/12
(52) U.S. Cl. .............. 436/546; 435/188; 436/524; 436/529; 436/530; 436/531; 530/391.1; 530/402; 530/409; 544/113; 544/131; 544/133; 546/257; 548/192; 548/265.4
(58) Field of Search .................. 544/133, 113, 544/131; 546/257; 548/265.4, 192; 436/546, 530, 529, 524, 531; 435/188; 530/402, 409, 391.1

(56) References Cited

U.S. PATENT DOCUMENTS

| | | |
|---|---|---|
| 4,687,659 | 8/1987 | Quay . |
| 4,722,892 | 2/1988 | Meares . |
| 5,476,939 | 12/1995 | Johnson . |
| 5,631,172 | 5/1997 | Johnson . |

FOREIGN PATENT DOCUMENTS

| | | |
|---|---|---|
| WO90/10709 | 9/1990 | (WO) . |
| WO 95/00845 | 1/1995 | (WO) . |

OTHER PUBLICATIONS

Blake, D. A., et al., "Metal Binding Properties of a Monoclonal Antibody Directed Toward Metal–Chelate Complexes", *J. Biol. Chem.*, 271(44): 27677–27685 (1996).

Brinkley, M., "A Brief Survey of Methods for Preparing Protein Conjugates with Dyes, Haptens, and Cross–Linking Reagents", *Bioconjugate Chem.*, 3 :2–13 (1992).

Chakrabarti, P. , et al., "Enzyme Immunoassay to Determine Heavy Metals Using Antibodies to Specific Metal–EDTA Complexes: Optimization and Validation of an Immunoassay for Soluble Indium", *Analy. Biochem.*, 217: 70–75 (1994).

Cochran, A. G., et al., "Antibody–Catalyzed Porphyrin Metallation", *Science*, 249:781–83 (1990).

Dandliker, W.B., et al. "Fluorescence Polarization Immunoassay. Theory and Experimental Method", *Immunochem.*, 10:219–227 (1973).

Franklin, S. J. , et al., "Solution Structure and Dynamics of Lanthanide Complexes of the Macrocyclic Polyamino Carboxylate DTPA–dien. NMR Study and Crystal Structures of the Lanthanum (III) and Europium (III) Complexes", *Inorg. Chem.*, 33:5794–5804 (1994).

Ghosh, P., et al., "Using Antibodies to Perturb the Coordination Sphere of a Transition Metal Complex", *Nature*, 382: 339–341 (1996).

Gillete, R. W., et al., "Development and Characterization of Monoclonal Antibodies with Specificity for Metallic Radioisotope Chelators Linked to Antibodies and Other Proteins", *J. Immunol. Methods*, 124: 277–82 (1989).

Goodwin, D. A., et al., "Pre–Targeted Immunoscintigraphy of Murine Tumors with Indium–111–Labeled Bifunctional Haptens", *J. Nucl. Med.*, 29:226–34 (1988).

Keinan, E., et al., "Toward Antibody–Mediated Metallo–Porphyrin Chemistry", *Pure & Appl. Chem.*, 62:2013–19 (1990).

Kosmas, C., et al., "Development of Humoral Immune Responses Against a Macrocyclic Chelating Agent (DOTA) in Cancer Patients Receiving Radioimmunoconjugates for Imaging and Therapy", *Cancer Res.*, 52:904–11 (1992).

Le Doussal, J–M., et al., "Targeting of Indium 111–Labeled Bivalent Hapten to Human Melanoma Mediated by Bispecific Monoclonal Antibody Conjugates: Imaging of Tumors Hosted by Nude Mice", *Cancer Res.*, 50:3445–52 (1990).

Li, M., et al., "Amine–Reactive Forms of a Luminescent Diethylenetriaminepentaacetic Acid Chelate of Terbium and Europium: Attachement to DNA and Energy Transfer Measurements", *Bioconjugate Chem.*, 8: 127–132 (1997).

Pietersz, G. A. , "The Linkage of Cytotoxic Drugs to Monoclonal Antibodies for the Treatment of Cancer", *Bioconjugate Chem.*, 1 (2):89–95 (1990).

Schwabacher, A. W., et al., "Metalloselective Anti–Porphyrin Monoclonal Antibodies", *J. Am. Chem. Soc.*, 111:2344–46 (1989).

Van Emon, J. M. et. al., "A Status Report on Field–Portable Immunoassay", *Environ. Science & Tech.*, 29(7): 312A–317A (1995).

Zöller, M., et al., "Establishment and Characterization of Monoclonal Antibodies Against an Octahedral Gallium Chelate Suitable for Immunoscintigraphy with PET", *J. Nucl. Med.*, 33(7):1366–72(1992).

*Primary Examiner*—Mary E. Ceperley
(74) *Attorney, Agent, or Firm*—Wean Khing Wong

(57) ABSTRACT

The present invention relates to the field of immunoassays for metal ions. The invention presents: chelators, chelates, antibodies specific for the chelates, tracers comprising chelates conjugated to detectable labels, and immunoassays utilizing the foregoing.

19 Claims, 11 Drawing Sheets

(SM 1)

$R_1-NH_2$ (A)

$P-NH_2$ (G)

(A) + Q—NH$_2$ (D)

(i)

$R_3$ is $-CH_3$; $-C(CH_3)_2CO_2{}^tBu$ (ii)

(iii)

(iv)

(v)

(vi)

DIETHYLENETRIAMINE-N,N',N"-TRIACETIC ACID DERIVATIVES

This patent application is based on U.S. Provisional Patent Application Serial No. 60/058,114, filed Sep. 5, 1997, entitled "Novel Diethylenetriamine-N,N',N"-Triacetic Acid Derivatives" of David K. Johnson.

FIELD OF THE INVENTION

The present invention relates to the field of immunoassays for metal ions based on biological binding agents that selectively recognize and bind chelated forms of the metal ions.

BACKGROUND OF THE INVENTION

Molecules that contain two or more atoms capable of forming donor (i.e., coordinate) bonds to a single metal atom are termed chelating agents, or chelators, and the corresponding metal complexes are called chelates. The number of donor atoms present in a chelator is termed its denticity.

The chemical abbreviations used in this application are according to the Periodic Table.

The first anti-chelate antibody was described by Meares, et al., U.S. Pat. No. 4,722,892. Subsequent disclosures have described monoclonal antibodies raised against the cobalt (II) complex of ethylenediaminetetraacetic acid (EDTA) [Goodwin, et al., *J. Nucl. Med.*, 29:226–34 (1988)], indium (III) complexes of diethylenetriaminepentaacetic acid (DTPA) [Gillette, et al., *J. Immunol. Methods*, 124:277–82 (1989); Le Doussal, et al., *Cancer Res.*, 50:3445–52 (1990)], iron (III) and cobalt (II) complexes of meso-tetrakis (carboxyphenyl)porphyrin [Schwabacher, et al., *J. Am. Chem. Soc.*, 111:2344–46 (1989)], N-methylmesoporphyrin IX [Cochran, et al., *Science*, 249:781–83 (1990)], the tin (IV) complex of meso-tetrakis(4-carboxyvinylphenyl) porphyrin [Keinan, et al., *Pure Appl. Chem.*, 62:2013–19 (1990)] and the gallium (III) complex of HBED [Zöller, et al., *J. Nucl. Med.*, 33:1366–72(1992)]. Blake et al., [*J. Biol. Chem.*, 271:27677–85 (1996)] disclose a monoclonal antibody, 2A8165, raised against a benzyl-EDTA complex of cadmium (II). The 2A81G5 antibody binds to the cadmium (II) complex of EDTA with good affinity, but also binds to the mercury (II) complex of EDTA with slightly higher affinity and to the EDTA chelates of indium (III) and manganese (II) with affinities only 3-fold and 5-fold lower, respectively, than that for Cd-EDTA. U.S. Pat. Nos. 5,476, 939 and 5,631,172 of Johnson describe certain chelators, chelates, labelled tracers, antibodies directed to the chelates, and immunoassays using the antibodies and tracers. In particular, U.S. Pat. No. 5,476,939 discloses chelators derived from pyridyl and isoquinolyl carbinolamines. In addition to these premeditated efforts, a polyclonal humoral anti-chelate response has been documented in some cancer patients receiving intravenous infusions of a monoclonal antibody conjugated to the yttrium (III) chelate of 1,4,7,10-tetraazacyclododecance-N, N',N"-tetraacetic acid (DOTA), a macrocyclic polyaminopolycarboxylate chelator [Kosmas, et al., *Cancer Res.*, 52:904–11 (1992)].

Chakrabarti et al., [*Anal. Biochem.*, 217:70–75 (1994)] disclose the use of an indium-specific monoclonal antibody in an enzyme linked immunosorbent assay (ELISA) for indium (III). Wagner et al., WO9010709, disclose monoclonal antibodies raised against mercury (II) and lead (II) complexes of the naturally occurring chelator glutathione and their use in heterogeneous immunoassays for these metal ions.

Quay, U.S. Pat. No. 4,687,659, discloses reaction of the cyclic dianhydride of diethylenetriaminepentaacetic acid (DTPA) with alkyl amines to give diethylenetriamine-N, N', N"-triacetic acid (DTTA) diaminde derivatives used to prepare magnetic resonance image (MRI) contrast agents. Franklin et al., [*Inorg. Chem.*, 33:5794 (1994)] disclose reaction of the cyclic dianhydride of DTPA with a diamine to give a cyclic diamide of DTTA. Li et al., [*Bioconjugate Chem.*, 8:127–132 (1997)] disclose the step-wise reaction of the cyclic dianhydride of DTPA with various alkyl and aryl amines to give luminescent bifunctional lanthanide chelates.

Fluorescent polarization techniques are based on the principle that a fluorescent labelled compound when excited by linearly polarized light will emit fluorescence having a degree of polarization inversely related to its rate of rotation. Therefore, when a fluorescent labelled tracer-antibody complex is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescent polarization provides a quantitative means for measuring the amount of tracer-antibody conjugate produced in a competitive binding immunoassay.

The fluorescent polarization technique was first applied to antibody-antigen interaction by Dandliker et al. [*Immunochem.*, 7:799–828 (1970); and *Immunol. Chem.*, 10:219–227 (1973)]. Examples of commercially available fluorescence polarization instruments are: IMx® and Tdx® analyzers (from Abbott Laboratories, Abbott Park, Ill.) and analyzers from Panvera, Inc., Madison, Wis. None of these are specifically directed to the detection or quantification of metal ions.

SUMMARY OF THE INVENTION

One aspect of the invention presents novel bifunctional chelators which incorporate an aromatic moiety that contains one or more metal binding sites.

Another aspect of the invention presents chelates formed from the above chelators complexed to one or more metal ions.

Another aspect of the invention presents the above chelators and chelates covalently linked to a macromolecular carrier, the resulting conjugate being immunogenic.

Another aspect of the invention presents a method for using the above immunogenic conjugate for the production of antibodies that are specific for the particular chelate and bind to it, preferably with high affinity. Also presented are the resulting antibodies.

Another aspect of the invention presents the above chelate covalently linked to a detectable label (hereinafter referred to as "label"), such as a fluorophore, to produce a detectable tracer molecule, such as a fluorescent tracer molecule.

Another aspect of the invention presents the above bifunctional chelators in unconjugated form, for use in the pretreatment of metal-containing samples to convert the metal ion present in the sample into the chelated form specifically recognized by the antibody.

Another aspect of the invention presents a method in which the above antibodies and tracers are used in an assay, preferably an immunoassay, that can detect and quantitate the metal ion of interest in the form of its chelate. Also presented are kits for conducting the above assays.

Another aspect of the invention presents methods for scavenging for metal ions in a sample and for removing metal ions from a sample.

Another aspect of the invention presents the above chelators or antibodies bound to a solid phase which are useful for the detection, quantification, scavenging, or removal of metal ions from a sample. The detection, quantification, scavenging, and removal methods are also presented.

Other aspects and advantages of the invention will be apparent to those skilled in the art upon consideration of the following detailed description which provides illustrations of the invention in its presently preferred embodiments.

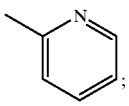

and conjugates (G) wherein P is a macromolecular carrier, a label or a solid phase.

Figure 1:
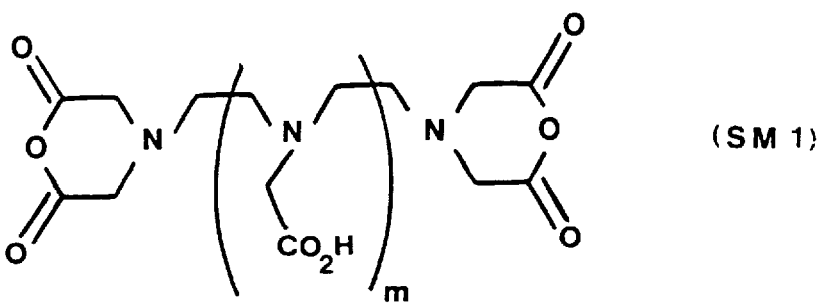
FIG. 1 presents the synthesis of chelators (A) wherein m can be 0 or 1 and $R_1$ has the structure shown, wherein (a) is any combination of carbon, nitrogen or sulfur atoms needed to complete a 5-, 6-, or 7- membered aromatic ring and $R_2$ is selected from substituents consisting of: $—CO_2H$, $—CH_2CO_2H$, $—C(=N—OR_3)CO_2H$ wherein $R_3$ may be $—CH_3$ or $—C(CH_3)_2CO_2{}^tBu$, $—SH$, $—CH_2SH$.
Figure 1:
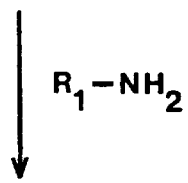
Figure 1:
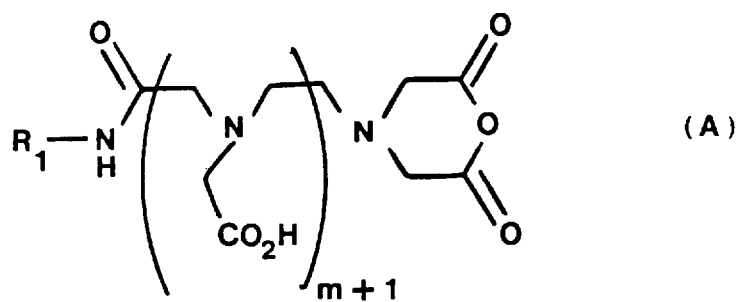
Figure 1:
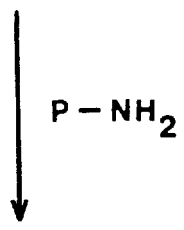
Figure 1:
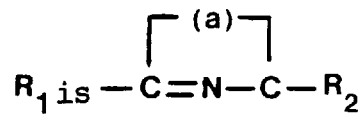
Figure 1:
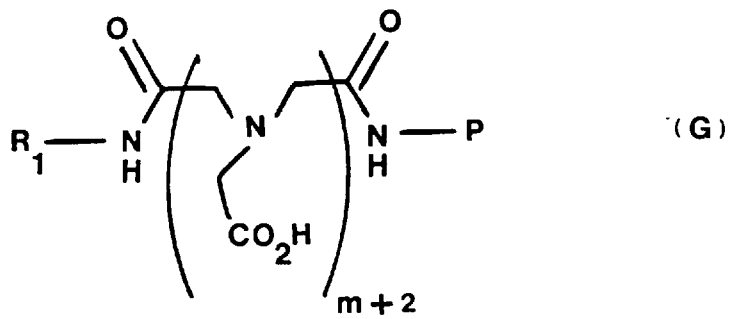
Figure 2:
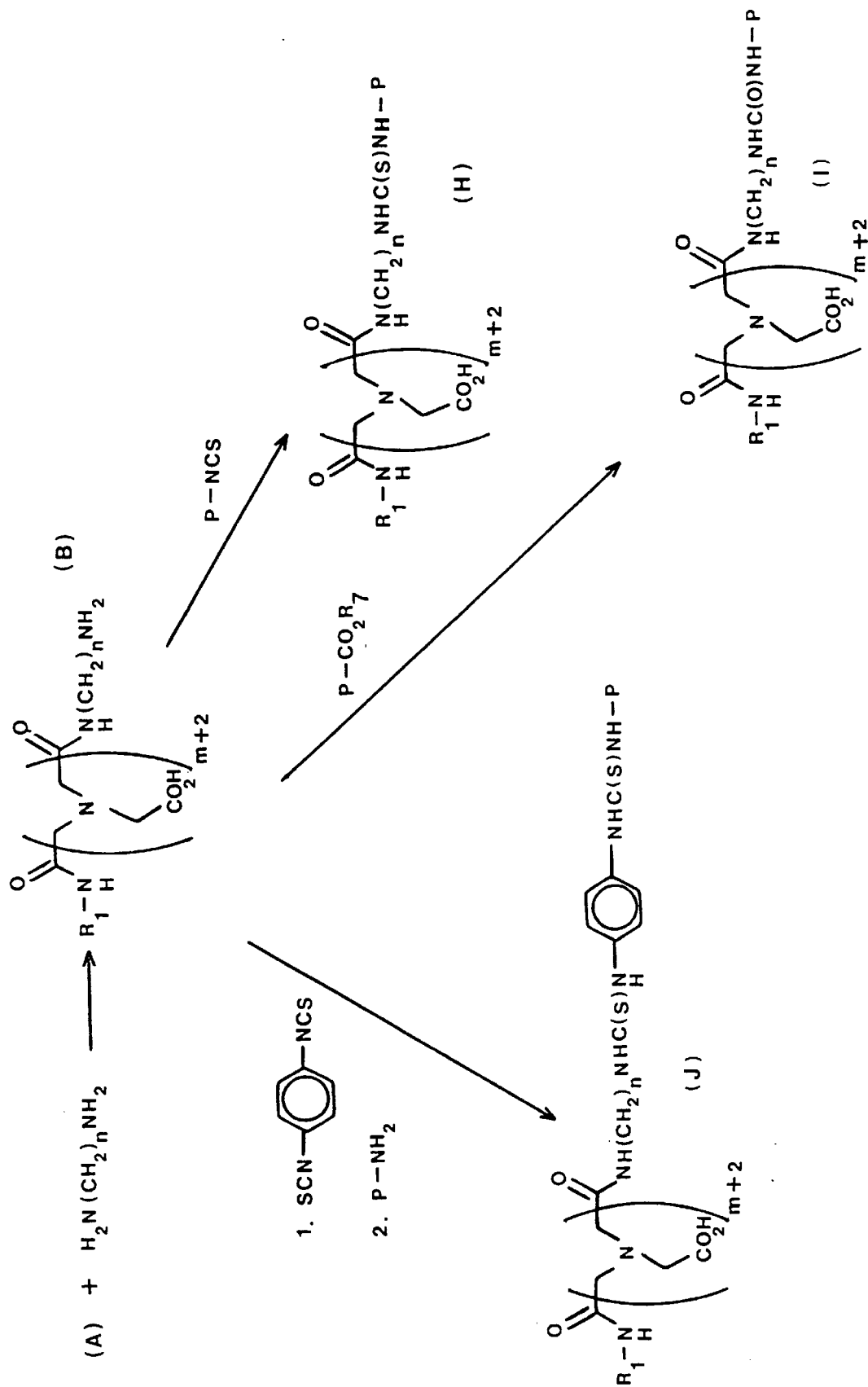

FIG. 2 presents the synthesis of chelators (B), and conjugates (H), (I), and (J). m and $R_1$ are as defined in FIG. 1 and $—CO_2R_7$ denotes an N-hydroxy-succinimidyl ester. P is as defined in FIG. 1.

Figure 3:
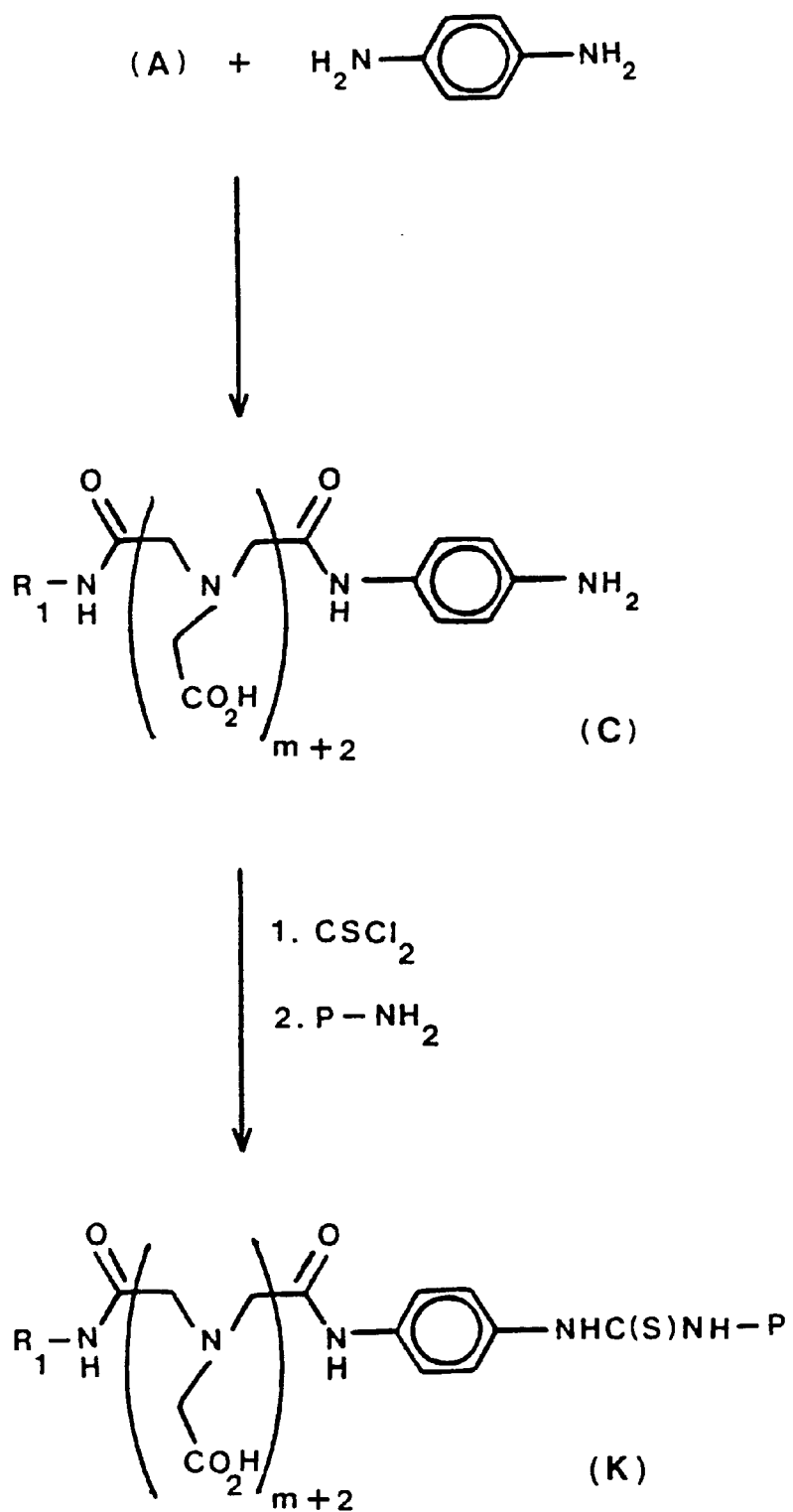

FIG. 3 presents the synthesis of chelators (C) and conjugates (K). P, m, and $R_1$, are as defined in FIG. 1.

Figure 4:
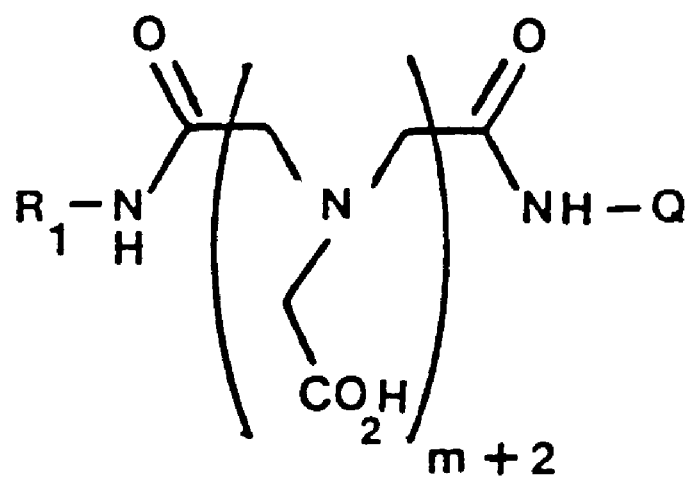

FIG. 4 presents chelators (D) wherein m and $R_1$ are as defined in FIG. 1 and Q is an alkyl, aryl, sulfonated alkyl or sulfonated aryl.

Figure 5:
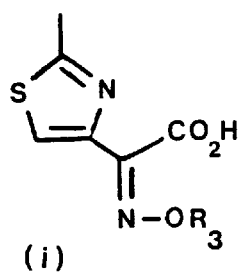
Figure 5:
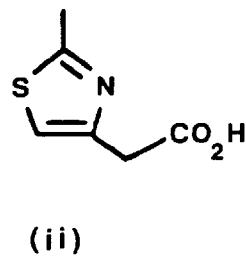
Figure 5:
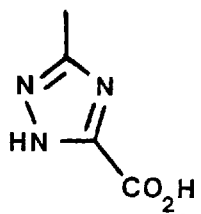
Figure 5:
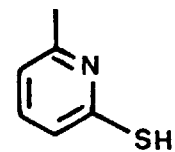
Figure 5:
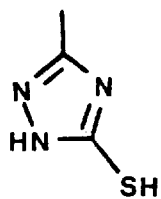
Figure 5:
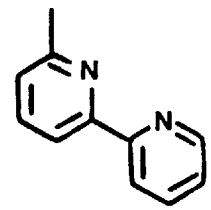

FIG. 5 presents a group of preferred structures for $R_1$.

Figure 6:
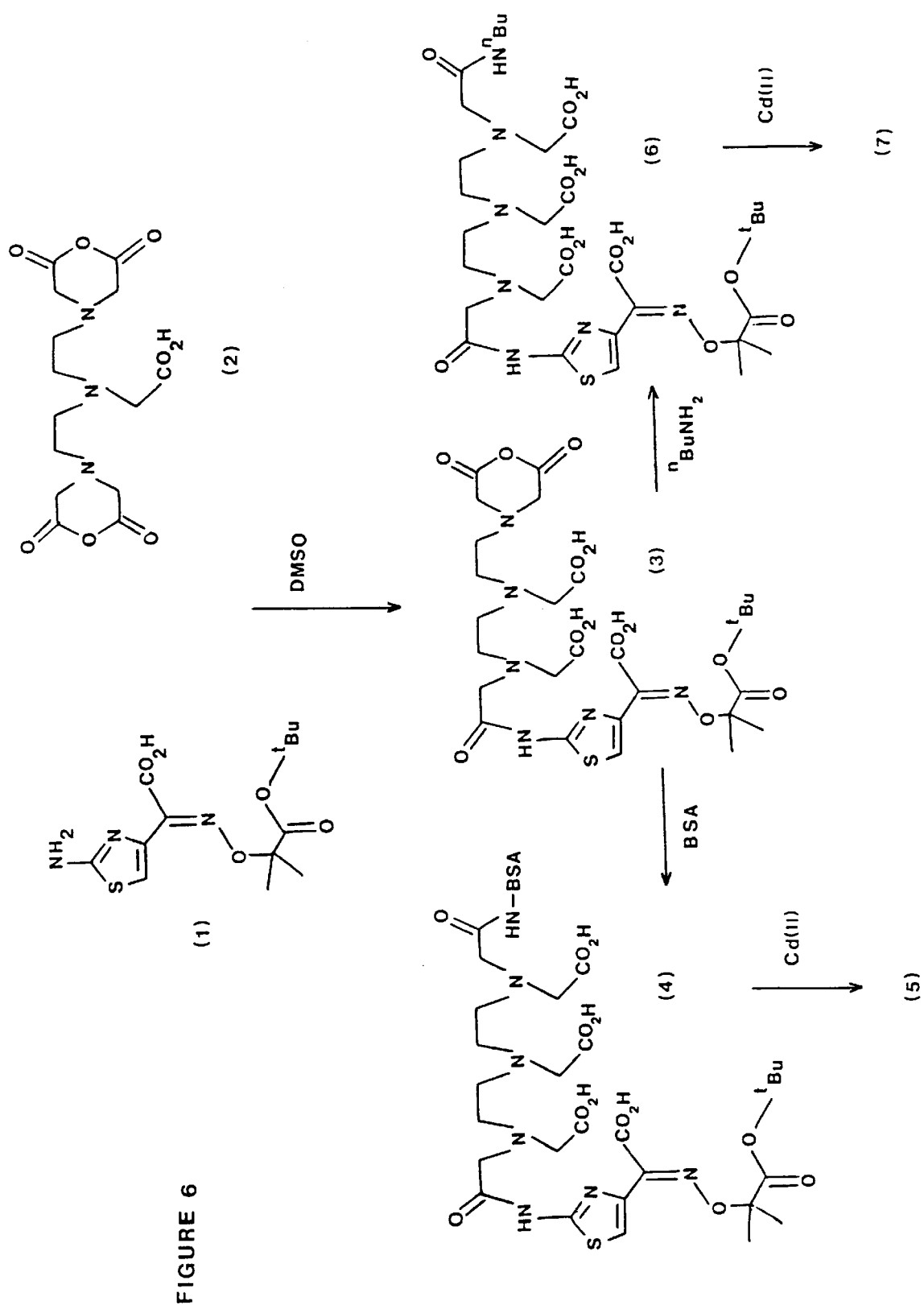

FIG. 6 presents the synthesis of the particularly preferred chelators (3) and (6), a particularly preferred BSA conjugate (4), and corresponding cadmium (II) chelates (7) and (5).

Figure 7:
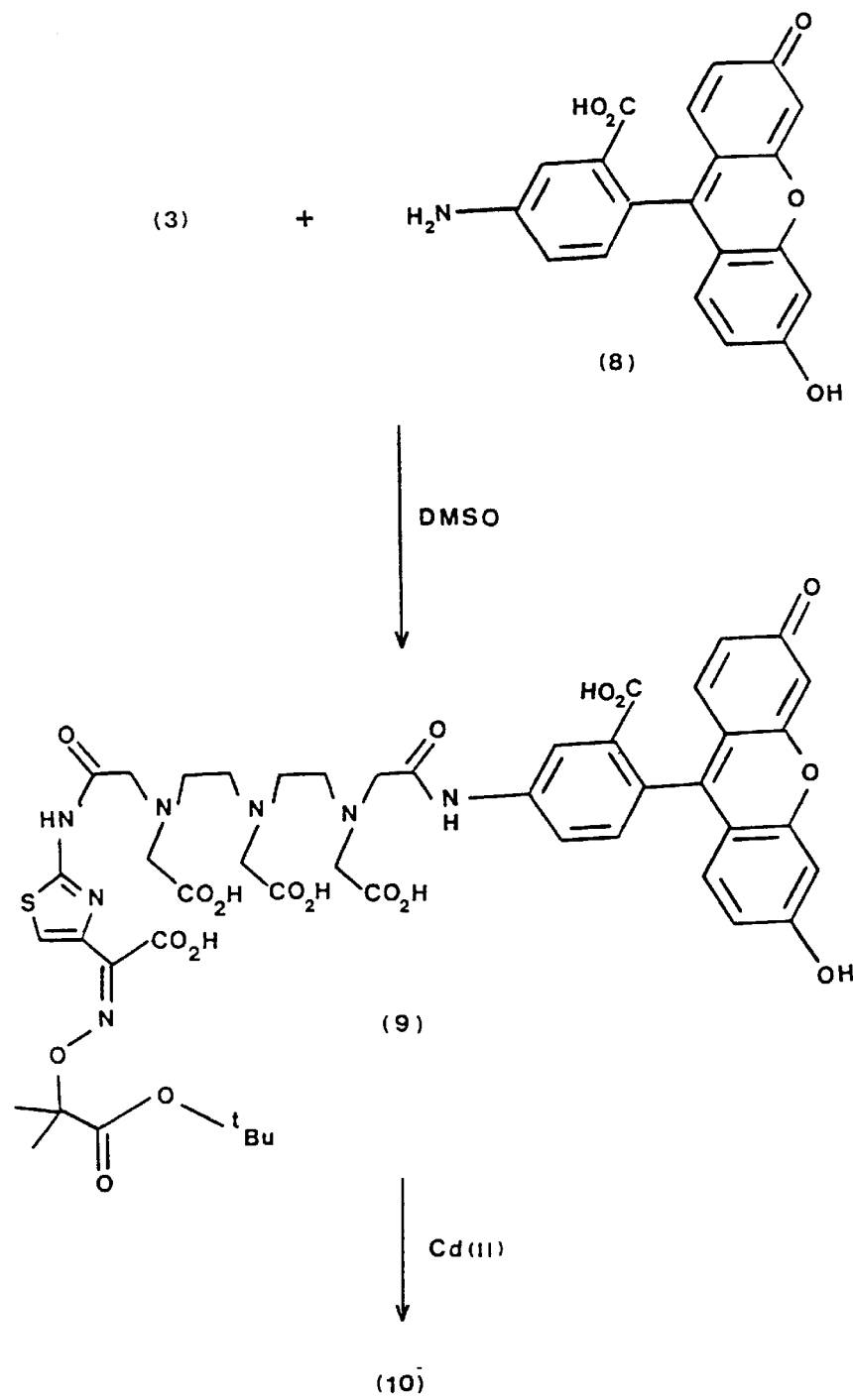

FIG. 7 presents the synthesis of a particularly preferred fluorescein-chelator conjugate (9) and the corresponding cadmium (II) chelate (10).

Figure 8:
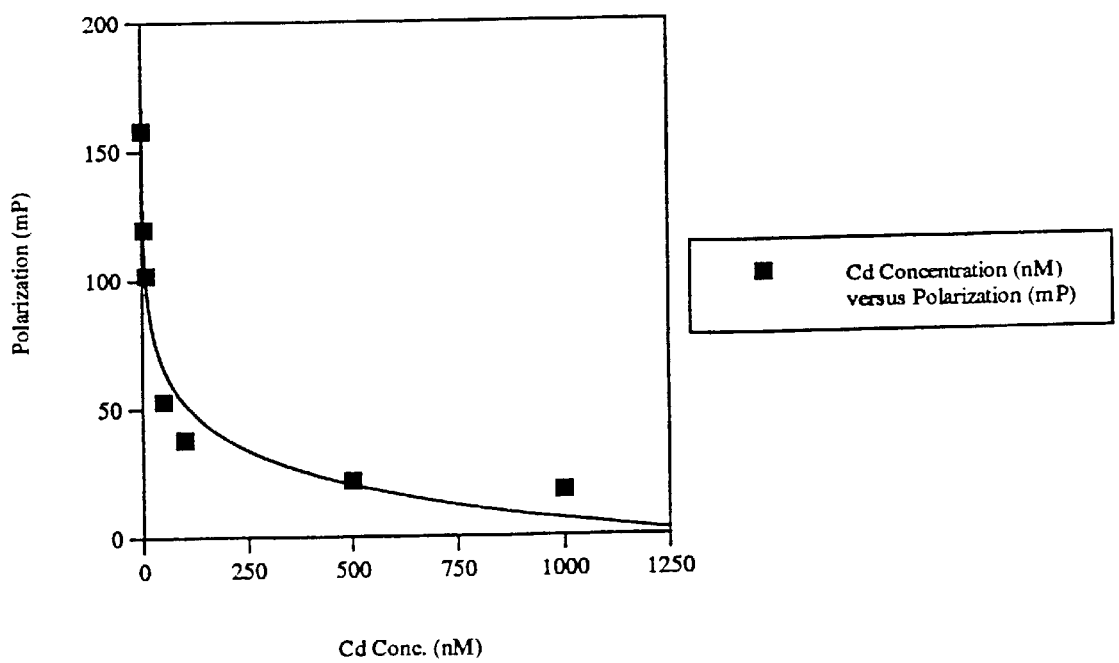

FIG. 8 graphically presents the data plotted as a standard curve that relates the concentration of cadmium chelate [(7) of FIG. 6] to the blank-subtracted fluorescence polarization of the sample, expressed in milli-polarization units (mP).

Figure 9:
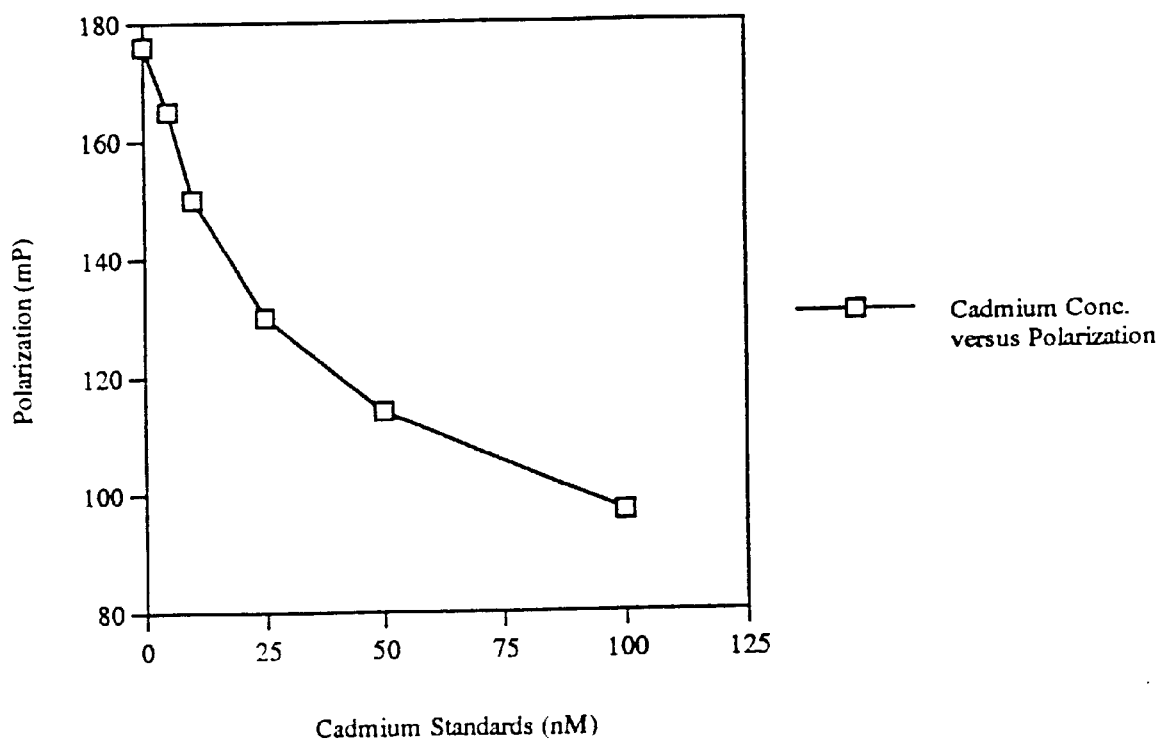

FIG. 9 graphically presents the fluorescence polarization of each cadmium chelate standard, excess chelator being added to each tube prior to addition of tracer and antibody.

Figure 10:
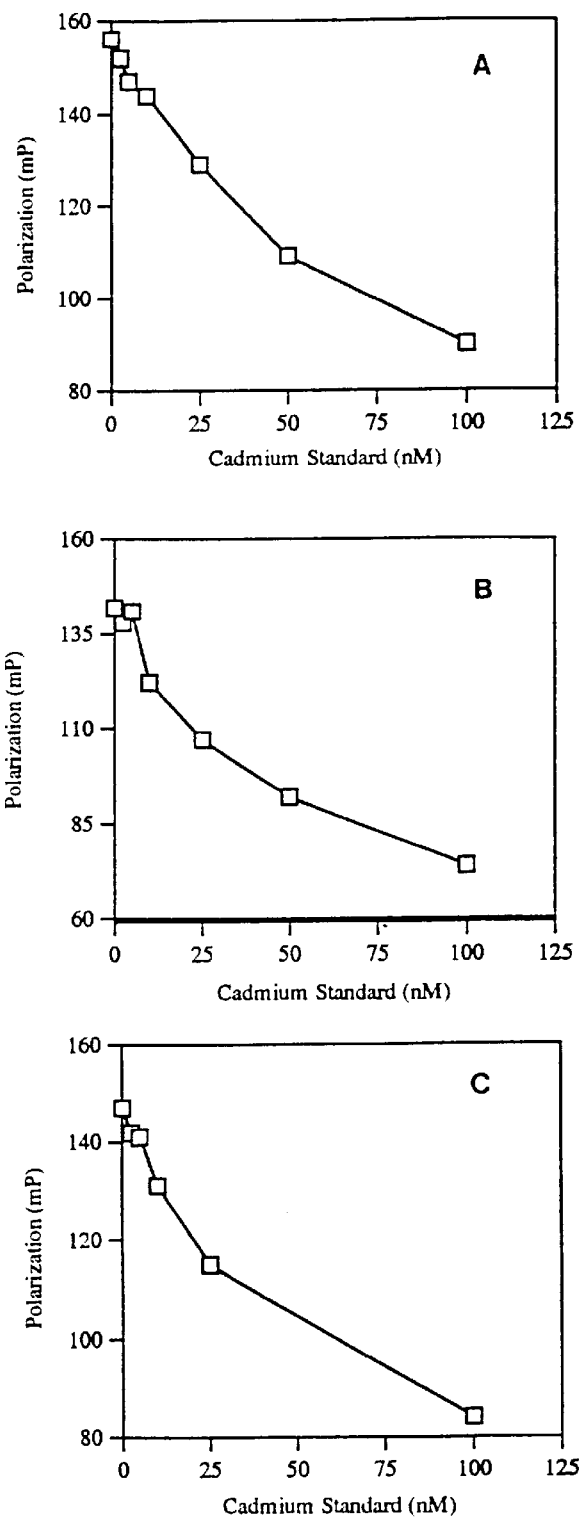

FIG. 10 graphically presents the fluorescence polarization of each cadmium chelate standard, wherein prior to the addition of tracer and antibody, (A) copper chelate, (B) mercury chelate, or (C) zinc chelate stock was added to each tube.

Figure 11:
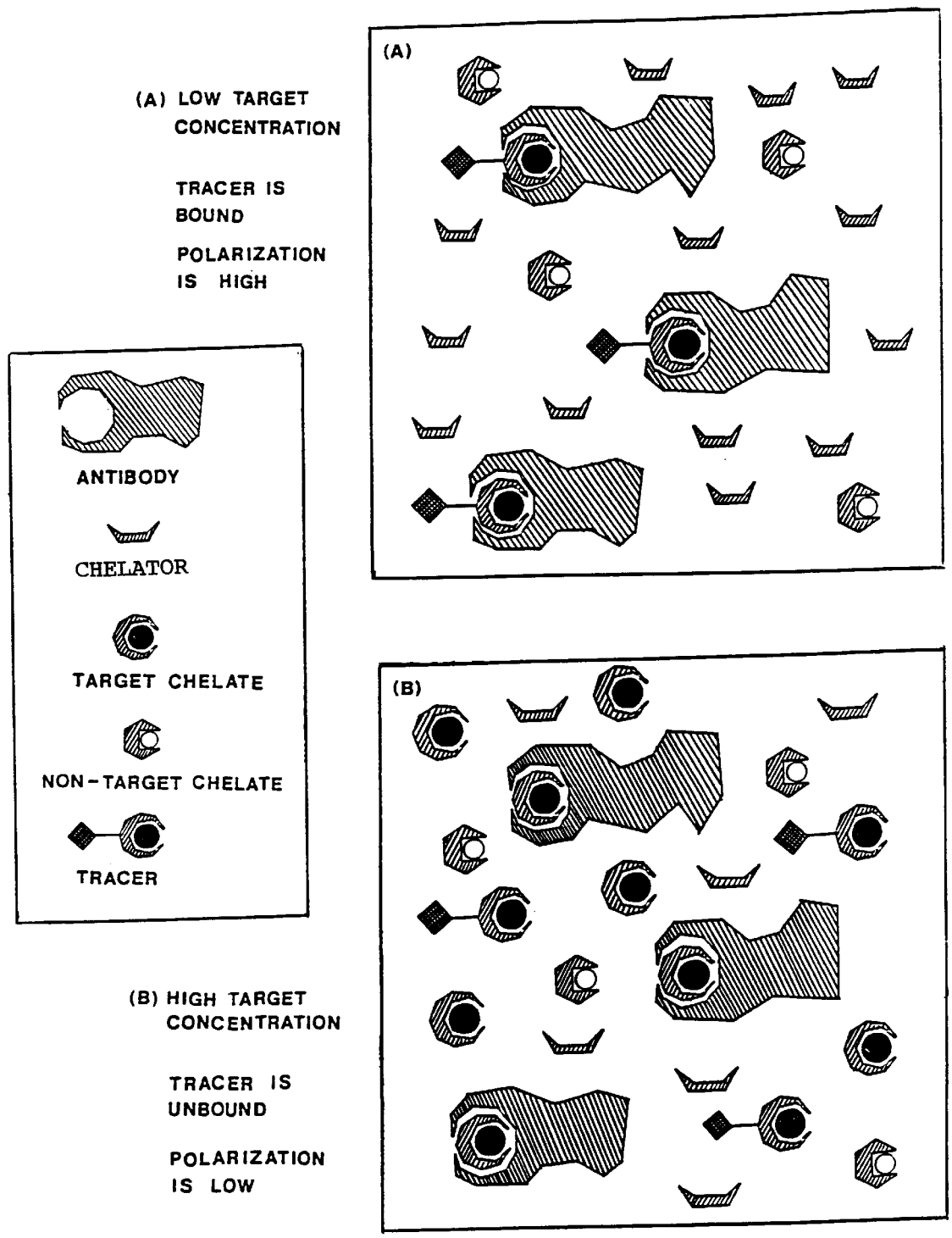

FIG. 11 presents a schematic of an immunoassay configuration. Two states are illustrated: (A) a sample containing no target metal ions; and (B) a sample containing high concentration of target metal ions.

DETAILED DESCRIPTION OF THE INVENTION

The present invention presents novel chelators and chelates. Chelates formed by combining a chelator of this invention with a given metal ion are useful as targets for generating biological binding agents that display specificity for that metal ion when presented in the form of said chelate. In particular, this invention relates to raising antibodies against "broad spectrum" synthetic chelates with a view to maximizing metal ion specificity and the use of these antibodies in immunoassays. The chelators of the present invention are "broad spectrum" in that, in common with other linear, high denticity polyaminopolycarboxylate chelators, such as ethylenediaminetetraacetic acid (EDTA), they are generally not themselves metal ion selective, but rather bind with high affinity to a wide range of metal ions.

The chelates preferably display molecular shape that is dependent on the nature of the particular metal ion present, providing a basis for metal ion specificity of biological binding agents that bind said chelates. For ease of discussion, the following uses antibodies, which are non-limiting examples of the biological binding agents, to illustrate the invention.

Antibodies according to the present invention can recognize and therefore bind different chelates of the same chelator because the intrinsic characteristics of metal ions (e.g., their valence, electronic charge, ionic radius, preferred coordination number, preferred coordination geometry, charge radius ratio, etc) are different for each metal ion, resulting in three-dimensional chelate shapes that, in their fine structural detail, are also unique to each metal. In addition to recognizing differences in chelate shape, the antibodies of this invention may also interact directly with the metal ion by formation of one or more coordinate bonds to amino acid side chains in the antibody binding site, although this is not a prerequisite for obtaining antibodies that are specific for a given chelate.

The preferred antibodies of the present invention bind with high affinity to the target chelate, irrespective of whether it is in conjugated form (i.e., covalently linked to another moiety such as a macromolecular carrier, a label such as a fluorophore or solid phase) or in unconjugated form. Conversely, they bind with low affinity, if at all, to the corresponding chelator and to chelates of non-target metal ions, again irrespective of whether said chelator and non-target chelates are in conjugated or unconjugated form.

In a preferred assay configuration, an antibody of the present invention is used in a competitive binding assay that monitors specific displacement of a fluorophore-conjugated target chelate (i.e., a tracer) by unconjugated target chelate, produced by treating the test sample with unconjugated chelator.

The chelators and biological binding agents can be used to detect and/or quantify metal ions in a test sample such as an aqueous sample (the latter is herein also referred to as "test solution"). Non-limiting examples of such samples include water samples, such as drinking water, freshwater, groundwater and wastewater that must be monitored for the presence of toxic metal ions such as mercury, lead, cadmium, chromium, etc., and process water, i.e., water used in an industrial process that must be monitored for metal contaminants that affect that process. Aqueous samples may also originate from more complex sample matrices such as sewage sludges, soil samples, particulate air samples, foods and food components, plant tissues and mammalian tissues, such as blood, serum, muscle, liver, bone, etc. Such complex sample matrices and solid or semi-solid test samples are generally subjected to either an extraction procedure or a digestion procedure to release metal ions present in the sample into an aqueous solution phase. This can, for example, be accomplished using methods known in the art. Such a solution phase often contains one or more strong acids such as $HNO_3$, HCl, $HClO_4$, etc., which is preferably neutralized prior to conducting the immunoassay. Such samples may be monitored for any of a variety of metal ions including toxic metal ions, metal ions endogenous in biological systems, metal ions administered as therapeutics, and precious metal ions. This subject is further discussed below.

The chelators and biological binding agents can also be used to extract and recover metal ions from the foregoing aqueous samples, e.g., to recover metal ions such as gold, silver and platinum from process streams and other sources. These metal ions may thus be extracted, refined, and/or recycled.

The following describes the invention in more detail.

I. Metal Ions of Interest

The present invention may be applied to any chelatable metal ions. Non-limiting examples of metal ions of interest (such as the target metal ions to be detected or quantitate in the assay of a test sample) to the present invention include main group metal ions, transition metal ions, and rare earth (lanthanide and actinide) metal ions. Of particular interest are toxic metal ions that may be present in the environment and represent a threat to human health (non-limiting examples of which include mercury, lead, cadmium, chromium, nickel, zinc, and copper). Also of interest are metal ions that may be found in the human body, such as the blood stream. Such metal ions include endogenous, essential metal ions and nonphysiologic metal ions that may be present either as a result of their use as therapeutics or because of ingestion, absorption or inhalation of metal ions present in the environment. Thus, the metal ions include lead, mercury, nickel, cadmium, thallium, antimony, silver, chromium, manganese, platinum, gold, aluminum, bismuth, gallium, iron, copper, zinc, cobalt, molybdenum, selenium, and vanadium ions.

In industrial applications, the metal ions of interest include metal ions present as contaminants in manufacturing processes, such as process streams (non-limiting examples of which include aluminum, iron, zinc, titanium and copper); and precious metal ions that are refined and/or recycled (non-limiting examples of which include gold, silver, platinum, iridium, rhodium, gallium and vanadium).

II. Chelators

Chelators of the present invention are preferably bifunctional, i.e., they contain, in addition to the chelator moiety, a side chain bearing an additional functionality through which the chelator may be covalently linked to a second moiety, denoted as P in the figures. Examples of P are labels, macromolecular carriers, solid phases, etc. In the figures, the chelators are represented as (A), (B), (C), (D), and additional chelators are (E) and (F) described further below. In the figures, the chelators that are covalently linked to a second moiety are represented as (G), (H), (I), (J), and (K).

This invention provides bifunctional chelators in two forms: those [e.g., chelator (A) of FIG. 1] that contain a highly reactive side chain substituent capable of directly forming a covalent bond with unmodified P; and those [e.g., chelator (B) of FIG. 2] that contain a relatively stable side chain substituent that is not itself reactive with unmodified P. The starting materials [(SM 1) and ($R_1$—$NH_2$) of FIG. 1] for making the chelators are commercially available or can be synthesized using methods known in the art.

Chelators of type (A) (FIG. 1) contain an anhydride function that is highly reactive with primary amine groups on other molecules, a reaction that produces an intermolecular amide linkage and a carboxymethylamine substituent that becomes part of the chelator structure in the resulting conjugate [(G), FIG. 1]. Procedures for using such a reaction scheme to produce immunogens and tracer conjugates are described in greater detail in the "EXAMPLES" section below. Because the anhydride moiety is highly reactive, it is undesirable to store such chelators for extended periods as they tend to lose reactivity due to hydrolysis. Chelators of type (A) are therefore most useful in applications where they can be synthesized and conjugated in one uninterrupted reaction sequence, without extensive handling or prolonged storage of the chelator itself.

For those applications where a more stable form of bifunctional chelator is desirable, and in situations where anhydride coupling chemistry is not appropriate (e.g., conjugation to a molecule that lacks primary amine groups) chelators such as (B) (FIG. 2) and (C) (FIG. 3) are provided. These structures contain a side chain that terminates in an aliphatic (B) or aromatic (C) primary amine group. The latter function can be further elaborated, using any of a wide variety of procedures well known to the art, to produce a covalent linkage to another molecule. Non-limiting examples of such procedures are shown in FIGS. 2 and 3, and disclosed by Brinkley [*Bioconjugate Chem.*, 3:2–13 (1992)] and by Pietersz [*Bioconjugate Chem.*, 1:89–95 (1990)]. The amine side chain can be reacted with amine-reactive functionalities incorporated into the conjugate partner molecule P to give conjugates of type (H) and (I) (FIG. 2). Further details of such a procedure, wherein an amine-reactive group (an isothiocyanate) on a label (fluorescein) is reacted with a chelator bearing an aliphatic amine side chain substituent to form a chelator-fluorescein conjugate, appear in EXAMPLE 11, below. Alternatively, the amine group on the side chain may be further derivatized to produce a highly reactive functionality, e.g., the aromatic amine moiety in (C) (FIG. 3) can be converted by methods well known in the art to an isothiocyanate function, which is spontaneously reactive with amine groups on other molecules such as proteins, giving conjugates (K) (FIG. 3). A third alternative is to use an additional molecule to link amine side chains on the chelator to functional groups on its conjugate partner molecule P, e.g., reaction with a bis(isothiocyanate) when P contains amine groups, to give conjugates (J) (FIG. 2). A preferred conjugation procedure for any given application will be readily apparent to one skilled in the art, based on the nature of the particular molecule to which the chelator is to be conjugated and the desired chemical properties and length of the side chain linking the chelator and P.

Of the two functions performed by a bifunctional chelator (chelation and linkage to another molecule), only the former is needed in structures to be used as sample pretreatment reagents. Such chelators (FIG. 4) are used to convert metal ions present in a given sample into a form that can be recognized by a biological binding agent. For these purposes, the side chain may contain no functional groups at all, terminating in, for example, alkyl or aryl groups [(D), FIG. 4] or it may incorporate functions intended to modify the physical properties of the molecule, such as inclusion of sulfonate groups to modify solubility.

A special case arises when one of the anhydride functions of a bis(anhydride) of the present invention is hydrolyzed while the other is converted to an amide. This produces the following chelators of formula (E):

wherein m can be 0 or 1 and $R_1$ is as defined in claim 1, below; and chelators of formula (F), shown below:

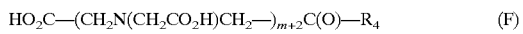

wherein m can be 0 or 1 and $R_4$ is as defined in claim 6, below.

Such chelators lack some of the structural features present in the parent structures (FIGS. 2 and 3) and employ a different combination of metal binding substituents. Nevertheless, they can be useful in some applications, e.g., as pre-treatment reagents.

Chelators useful in the present invention preferably contain a diethylenetriamine-N, N', N"-triacetic acid (DTTA) or ethylenediamine-N, N'-diacetic acid (EDDA) structure linked via an amide bond to an aromatic ring system that contains a ring N atom ortho to the amide attachment site and one or more additional ring substituents capable of binding to a metal, i.e., the ring substituents contain donor atoms. In general, the number of atoms linking adjacent donor atoms should be from 1 to 4, so that the resulting chelate rings are 4-, 5-, 6-, or 7-membered. In addition to metal binding substituents, the chelators may also contain additional substituents which are not directly involved in metal binding but which are tethered to substituents that do bind the metal. Preferred chelators have denticities of 5 and higher and form chelates of high stability with a wide range of metal ions.

A particularly preferred chelating structure is exemplified by (6) (FIG. 6). The structure contains eight donor atoms, comprising the three aliphatic N atoms, the aromatic N atom and four carboxylic oxygen atoms (one from each carboxyl group). The substituted thiazole ring provides a delocalized π-system that can become directly involved in binding to a metal ion via the ring N atom and/or the carboxyl group present on the ring substituent. The aliphatic side chain that is attached to the ring substituent via an imine linkage does not itself contain donor atoms, but it is tethered to the carboxyl ring substituent which can bind to a metal and thus may adopt conformations that are indirectly affected by metal ion binding.

(a) Further Non-Limiting Examples of Chelators and Chelates

The following are more non-limiting examples of chelators of the present invention:

The class of chelators, designated CHELATOR1 (this designation is also herein used to refer to a member of this class of chelators. This nomenclature applies to the other classes of chelators.), in which each chelator has the structure (A) as shown in FIG. 1, wherein: m is 0 or 1; $R_1$ has the structure shown in FIG. 1, wherein (a) is any combination of carbon, nitrogen, or sulfur atoms needed to complete a 5-, 6-, or 7- membered aromatic ring and $R_2$ is selected from the group of ring substituents consisting of: —$CO_2H$; —$CH_2CO_2H$; —SH; —$CH_2SH$;

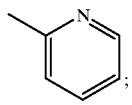

and —$C(=N-OR_3)CO_2H$, wherein $R_3$ is —$CH_3$ or —$C(CH_3)_2CO_2{}^tBu$.

The class of chelators, designated CHELATOR2, in which each chelator has the structure (A) of FIG. 1, wherein m is 0 or 1, and $R_1$ is selected from the group of ring systems consisting of structures (i) to (vi) of FIG. 5.

The class of chelators, designated CHELATOR3, in which each chelator has the structure (A) of FIG. 1, wherein m is 1 and $R_1$ is selected from the group consisting of structures (i) and (ii) of FIG. 5.

The class of chelators, designated CHELATOR4, in which each chelator has the structure shown below:

wherein $R_1$ has the structure shown in FIG. 1, wherein (a) in FIG. 1 is any combination of carbon, nitrogen, or sulfur atoms needed to complete a 5-, 6-, or 7- membered aromatic ring and $R_2$ is selected from the group of ring substituents consisting of: —$CO_2H$; —$CH_2CO_2H$; —SH; —$CH_2SH$; —σ—$C_6H_4N$; and —$C(=N-OR_3)CO_2H$, wherein $R_3$ is —$CH_3$ or —$C(CH_3)_2CO_2{}^tBU$. m is 0 or 1. $R_4$ is selected from the group consisting of: —NH—$(CH_2)_n$—$NH_2$, wherein n is a number from 1 to 10; —NH—ø—$NH_2$; —NH—ø—NCS; —NH—$(CH_2)_n$—NHC(S)NH—ø—NCS, wherein n is a number from 1 to 10; and —$NHR_5$, wherein $R_5$ is selected from the group consisting of: -alkyl having from one carbon to ten carbons; -aryl having from six carbons to twenty carbons; -sulfonated alkyl having from one carbon to ten carbons; and -sulfonated aryl having from six carbons to twenty carbons.

The preferred chelators of class CHELATOR4 are those having $R_1$ selected from the group consisting of structures (i) to (vi) of FIG. 5, and $R_4$ selected from the group consisting of: —NH—$(CH_2)_n$—$NH_2$, wherein n is a number from 1 to 10; —NH—ø—$NH_2$; and —$NHR_5$ wherein $R_5$ is selected from the group consisting of: -alkyl having from one carbon to ten carbons; and -aryl having from six carbons to twenty carbons.

Other preferred chelators of class CHELATOR4 are those wherein m is 1, $R_1$ is selected from the group consisting of structures (i) and (ii) of FIG. 5, and $R_4$ is selected from the group consisting of: —NH—$(CH_2)_6$—$NH_2$, and $NH^nBu$.

The class of chelators, designated CHELATOR5, in which each chelator has the structure represented by formula (E), below:

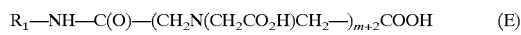

wherein m is 0 or 1. $R_1$ has the structure shown in FIG. 1, wherein (a) is any combination of carbon, nitrogen, or sulfur atoms needed to complete a 5-, 6-, or 7- membered aromatic ring and $R_2$ is selected from the group of ring substituents consisting of: —$CO_2H$; —$CH_2CO_2H$; —SH; —$CH_2SH$; —σ—$C_6H_4N$; and —$C(=N-OR_3)CO_2H$, wherein $R_3$ is —$CH_3$ or —$C(CH_3)_2CO_2{}^tBu$.

The class of chelators, designated CHELATOR6, in which each chelator has the structure represented by formula (F), below:

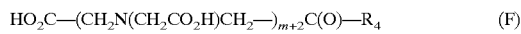

wherein m is 0 or 1. $R_4$ is selected from the group consisting of: —NH—$(CH_2)_n$—$NH_2$, wherein n is a number from 1 10; —NH—ø—$NH_2$; —NH—ø—NCS; —NH—$(CH_2)_n$—NHC(S)NH—ø—NCS, wherein n is a number from 1 to 10; and —$NHR_5$, wherein $R_5$ is selected from the group consisting of: -alkyl having from one carbon to ten carbons; -aryl having from six carbons to twenty carbons; -sulfonated alkyl having from one carbon to ten carbons; and- sulfonated aryl having from six carbons to twenty carbons.

Included in this invention are chelates formed by any of the chelators, of the present invention, complexed with one or more metal ions, preferably the metal ions of interest discussed in the section "I. Metal Ions of Interest", above. The preferred metal ions are transition metal or main group metal ions, the most preferred metal ions are cadmium (II) atoms. The preferred chelates are CHELATOR2, CHELATOR3, and CHELATOR4 complexed with one or more transition metal or main group metal ions. Also preferred is CHELATOR3 complexed with one or more cadmium (II) atoms. Further preferred is CHELATOR4 complexes with one or more cadmium (II) atoms, with the chelator having m equals to 1, $R_1$ selected from the group consisting of structures (i) and (ii) of FIG. 5, and $R_4$ selected from the group consisting of: —NH—$(CH_2)_6$—$NH_2$, and NH$^n$Bu.

III. Macromolecular Carrier-Chelate Conjugates Serving as Immunogens and Production of Biological Binding Agents Directed to Them According to another aspect of the present invention, immunogenic conjugates wherein chelates of the present invention are covalently linked to a macromolecular carrier (the macromolecular carrier is herein designated "X" in the chemical structures) are used to produce antibodies in animals exposed to them. Thus, the macromolecular carrier is preferably an immunogenic moiety. Any immunogenic moieties known in the art for provoking production of antibodies in animals may be used. Also included in the present invention are the resulting antibodies, which are further discussed in the section, "IV. Biological Binding Agents", below. The macromolecular carrier X can be selected from any of those conventionally known in the art. In most instances, the macromolecular carrier will be a protein, a polypeptide, or a peptide, although other materials such as carbohydrates, polysaccharides, lipopolysaccharides, poly (amino) acids, nucleic acids, and the like, can also be employed. Preferably, the macromolecular carrier is a protein such as bovine serum albumin (BSA), keyhole limpet hemocyanin (KLH), thyroglobulin, immunoglobulin (IgG), and the like. For ease of discussion, the following discussion uses protein to illustrate the macromolecular carrier, one skilled in the art would realize that other macromolecular carriers may be used in place of the protein. The methods for synthesizing the alternative chelate conjugates can be arrived at by one skilled in the art based on the disclosure herein.

The protein-chelate conjugates may be used as immunogens or as coatings for alternative enzyme-linked immunosorbent assay (ELISA) format assays for metal ions.

General methods for the preparation of protein-chelator conjugates are illustrated in FIGS. 1, 2, and 3; and the preparation of a particularly preferred BSA-chelator conjugate [structure (4) of FIG. 6] is described in detail in EXAMPLE 2, below. Such protein-chelator conjugates are converted into the corresponding chelate conjugates by treatment with the metal ion of interest, as illustrated in detail for a preferred metal [Cd(II)] in EXAMPLE 3, below.
(a) Further Non-Limiting Examples of the Macromolecular Carrier-Chelator Conjugates Thus, disclosed herein is a class of conjugates in which each member chelator is conjugated to a moiety such as macromolecular carriers, labels and solid phases. The chelator is selected from those disclosed in the present invention.

The following are non-limiting examples of other classes of conjugates, wherein X can be any of the macromolecular carriers described above:

The class of conjugates, designated CONJ1 (this designation is also herein used to refer to a member of this class of conjugates. This nomenclature applies to the other classes of conjugates.), each with a chelator covalently linked to a macromolecular carrier X and the conjugate has the following structure:

wherein m is 0 or 1; $R_1$ has the structure shown in FIG. 1, wherein (a) in FIG. 1 is any combination of carbon, nitrogen, or sulfur atoms needed to complete a 5-, 6-, or 7-membered aromatic ring and $R_2$ is selected from the group of ring substituents consisting of: —SH; —$CH_2SH$;

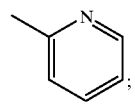

—$CO_2H$; —$CH_2CO_2H$; and —C(=N—$OR_3$)$CO_2H$, wherein $R_3$ is —$CH_3$ or —$C(CH_3)_2CO_2{}^tBU$. $R_6$ is selected from the group consisting of: —NH—; —NH—ø—NHC(S)NH—; —NH—$(CH_2)_n$—NH—C(O)—; —NH—$(CH_2)_n$—NH—C(S)—NH—; —NH—$(CH_2)_n$—NHC(S)NH—ø—NHC(S)NH—; wherein n is a number from 1 to 10.

The class of conjugates, designated CONJ4, each with a chelator covalently linked to a macromolecular carrier X and the conjugate has the following structure:

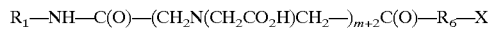

wherein X can be any of the macromolecular carriers described above. The preferred X is selected from the group consisting of: proteins, polypeptides, peptides, carbohydrates, polysaccharides, lipopolysaccharides, poly(amino acids), and nucleic acids. m is 0 or 1. $R_1$ is as defined is selected from the group of ring systems consisting of structures (i) to (vi) of FIG. 5; and $R_6$ is selected from the group consisting of: —NH—; —NH—$(CH_2)_n$—NHC(S)NH—; and —NH—$(CH_2)_n$—NH—C(O)—, wherein n is a number from 1 to 10.

The class of conjugates, designated CONJ5, each with a chelator covalently linked to a macromolecular carrier X and the conjugate has the following structure:

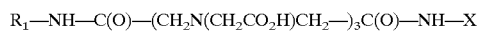

The preferred X is bovine serum albumin. $R_1$ is selected from the group consisting of structures (i) and (ii) of FIG. 5.

Also included in this invention are chelate-conjugates formed by any of the conjugates of the present invention complexed with one or more metal ions. The foregoing includes macromolecular carrier-chelate conjugates, label-chelate conjugates, and solid phase-chelate conjugates. Thus, the present invention includes a complex of conjugate CONJ1, CONJ2, CONJ3, CONJ4, CONJ5, CONJ6, CONJ7, CONJ8, or CONJ9, complexed with one or more metal ions. The metal ions are preferably the metal ions of interest discussed in the section "I. Metal Ions of Interest", above. The preferred metal ions are transition metal or main group metal ions, the most preferred metal ions are cadmium (II) ions. Thus, for example, the preferred complex is any complex formed by a member of CONJ4, CONJ5, CONJ6, CONJ7, CONJ8, and CONJ9 conjugate classes complexed with one or more transition and/or main group metal ions. The preferred metal ions are cadmium (II) ions.

IV. Biological Binding Agents

Another aspect of the present invention thus relates to biological binding agents that possess specific, high affinity binding sites for chelates, preferably chelates of the present invention. Preferred biological binding agents are antibodies specific for a given chelate, preferably obtained using immunogens in which the chelate is covalently coupled to a macromolecular carrier, which is preferably a protein, via a reactive side chain. In particular, these antibodies, either polyclonal, monoclonal, recombinant, etc (as further described below) selectively recognize a metal complex formed between a chelator of the present invention and any metal ion of interest. These antibodies are preferably produced by the immunogens discussed above. Unless otherwise indicated, antibodies herein include: polyclonal and monoclonal antibodies, monospecific antibodies, and antisera which includes monospecific antisera. Besides whole immunoglobulins, antibodies herein also include antigen binding fragments of the immunoglobulins. Examples of these fragments are Fab, F(ab')$_2$, and Fv. Such fragments can be produced by known methods. The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel et al., U.S. Pat. No. 4,676,980.

The immunogens of the present invention can be used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen of the present invention which is normally in a mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques known in the art to obtain monoclonal antibodies, and can be stored, for example, at −20° C.

Monoclonal antibodies can be produced by the method of Köhler and Milstein [Nature, 256: 495–497 (1975)] by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps. In the present invention, the resulting hybridomas are screened for production of monoclonal antibodies that bind to the target chelates but do not bind to the chelator or to non-target chelates.

More specific methods for producing polyclonal and monoclonal antibodies specific to chelates have been described in the prior art (see the discussion in "Background of the Invention", above, the references cited therein are hereby incorporated by reference) and can be used for the production of polyclonal and monoclonal antibodies of this invention except that the immunogens for the desired antibodies would be as those described in this invention.

Without wishing to be bound by the hypothesis, it is hypothesized that the antibody recognition of a chelate is more specific when delocalized π-systems in the chelator structure can become directly involved in binding to the metal ion, as opposed to prior art antibody targets in which delocalized π-systems, if present at all, were part of the linkage to protein and thus were remote from, and largely uninfluenced by, the metal center. It is further hypothesized that incorporating into a chelator structural features, such as a hydrophobic side chain, that are not directly involved in metal binding but which may change conformation on chelation, may provide additional mechanisms for interactions with protein and contribute to metal ion specificity.

Of particular interest to the present invention are antibodies that selectively recognize chelates of cadmium (II) and a preferred embodiment of the invention provides an immunoassay for cadmium based on polyclonal anti-chelate antibodies recognizing the cadmium (II) complex (7) of FIG. 6 and EXAMPLE 7, below. One of the preferred biological binding agent is a polyclonal antibody population which recognizes the chelate comprising cadmium ions bound to a member of CHELATOR4 class, preferably the CHELATOR4 class has the following features: m is 1, $R_1$ is selected from the group consisting of structures (i) and (ii) of FIG. 5, and $R_4$ is selected from the group consisting of: —NH—$(CH_2)_6$—$NH_2$, and NH"Bu.

Antibodies raised against chelates of the present invention offer the advantage of high specificity for the target metal ion. Specific binding to the chelate of the target metal ion is achievable in the presence of excess non-target metal ion and/or excess chelator. This makes it possible to configure sensitive and specific immunoassays for a metal ion of interest, by adding an unconjugated form of a chelator of the present invention to a sample thought to contain the target metal ion, then using an antibody which recognizes the resulting chelate to probe for its presence. The surprisingly high degree of metal ion specificity exhibited by antibodies recognizing chelates of the present invention (such as shown in EXAMPLES 9 and 10, shown below.) is thought to reflect the inclusion of structural features that permit multiple mechanisms for interaction with protein (e.g., aromatic stacking, hydrophobic interactions) at positions in the chelate framework that are metal ion responsive. This increases the likelihood that a particular chelate shape exists that is unique to a given metal ion of interest. In addition, the use of sterically flexible chelating structures leaves open the possibility that the antibody binding site may contribute one or more donor atoms on amino acid side chains, although this is not essential for metal ion specificity to be observed. Thus, a rabbit polyclonal antibody raised against a cadmium (II) chelate of the present invention [such as shown in EXAMPLE 3, below, and structure (5) of FIG. 6] showed low cross-reactivity with mercury (II) such that a standard curve could be generated for differing concentrations of the cadmium chelate in the presence of a large fixed excess of the analogous Hg (II) complex. Not only was cross-reactivity low for Hg (II) (1–2%) but it was similarly low for Cu (II) and Zn (II)(as shown in EXAMPLE 10, below).

V. Label-Chelator Conjugates Serving as Tracer

Reaction sequences analogous to those used to prepare immunogens may be used to prepare conjugates that consist of a label (the label is herein designated "Y" in the chemical structures) covalently linked to the chelator at the same site used for linkage to the protein. Preferred labels (Y) are fluorescent compounds (i.e., fluorophores), enzymes, radioisotopes, chromophores, chemiluminescent molecules, phosphorescent molecules, and luminescent molecules. Non-limiting examples of fluorescent compounds are:

fluorescein, fluorescein derivatives that are amine reactive, rhodamine, pyrene, napthalenes, coumarins, and BODIPY™ dyes (Molecular Probes, Eugene, Oreg.). Fluorescein is particularly preferred.

General methods for the preparation of such fluorophore conjugates are shown in FIGS. 1, 2, and 3. Detailed procedures for the synthesis of two particularly preferred fluorescein conjugates, structure (9) (FIG. 7) and structure (H) [FIG. 2, wherein P is fluorescein, m is 1, n is 6, and $R_1$ has structure (i) of FIG. 5 in which $R_3$ is —C(CH$_3$)$_2$CO$_2^t$Bu] are given in EXAMPLES 5 and 11, respectively. Conversion of these preferred fluorescein-chelator conjugates to the corresponding Cd(II) chelates is described in detail in EXAMPLES 6 and 11, below.

(a) Further Non-Limiting Examples of Label-Chelator Conjugates

The following are further non-limiting examples of the label-chelator conjugates of the present invention:

The class of conjugates, designated CONJ2, each with a chelator covalently linked to a label "Y" and having the structure:

wherein Y can be any label described above. m is 0 or 1; $R_1$ has the structure shown in FIG. 1, wherein (a) in FIG. 1 is any combination of carbon, nitrogen, or sulfur atoms needed to complete a 5-, 6-, or 7-membered aromatic ring and $R_2$ is selected from the group of ring substituents consisting of: —CO$_2$H; —CH$_2$CO$_2$H; —SH; —CH$_2$SH;

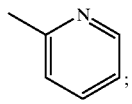

and —C(=N—OR$_3$)CO$_2$H, wherein $R_3$ is —CH$_3$ or —C(CH$_3$)$_2$CO$_2^t$Bu. $R_6$ is selected from the group consisting of: —NH—; —NH—ø—NHC(S)NH—; —NH—(CH$_2$)$_n$—NH—C(O)—; —NH—(CH$_2$)$_n$—NH—C(S)—NH—; —NH—(CH$_2$)$_n$—NHC(S)NH—ø—NHC(S)NH—; wherein n is a number from 1 to 10.

The class of conjugates, designated CONJ6, each with a chelator covalently linked to a label "Y" and having the structure:

wherein Y can be any of the labels described above. m is 0 or 1. $R_1$ is selected from the group of ring systems consisting of structures (i) to (vi) of FIG. 5. $R_6$ is selected from the group consisting of: —NH—; —NH—(CH$_2$)$_n$—NHC(S)NH—; and —NH—(CH$_2$)$_n$—NH—C(O)—, wherein n is a number from 1 to 10.

The class of conjugates, designated CONJ7, each with a chelator covalently linked to a label "Y" and having the structure:

wherein Y can be any of the labels described above, and is preferably a fluorophore, and more preferably a fluorescein. $R_1$ is selected from the group consisting of structures (i) and (ii) of FIG. 5. $R_6$ is selected from the group consisting of: —NH—; and —NH—(CH$_2$)$_6$—NHC(S)NH—.

VI. Anti-Chelate Antibody Screening Assays

The following assays may be used to monitor the polyclonal antibody response in a given animal and/or to screen for monoclonal antibodies.

Screening by fluorescence polarization may be performed by probing the test sample with a tracer containing the target chelate [e.g., structure (10) of FIG. 7]. Positive samples are characterized by a highly polarized signal relative to control samples containing non-specific antibody. Positive samples may be evaluated further for cross-reactivity by measuring the polarization of samples probed, under the same conditions, with tracers containing the chelator [e.g., structure (9) of FIG. 7] and non-target chelates [e.g., the Zn(II), Cu(II), and Hg(II) analogs of structure (10) of FIG. 7]. Antibodies are selected that give a highly polarized signal when probed with the target tracer and a relatively depolarized signal when probed with tracers containing the chelator or a non-target chelate.

Alternatively, protein conjugates such as structure (5) of FIG. 6 may be coated onto a solid phase (designated "Z" in the chemical structures), such as a microtiter plate, and used in ELISA format screening assays. Antibodies are selected that show high levels of binding to plates coated with a conjugate containing the target chelate [e.g., structure (5) of FIG. 6] and low levels of binding to plates coated with chelator conjugate [e.g., structure (4) of FIG. 6] and those coated with non-target chelate conjugates [e.g., Zn(II), Cu(II), and Hg(II) analogs of structure (5) of FIG. 6].

(a) Further Non-Limiting Examples of Chelators Covalently Linked to a Solid Phase The following are further non-limiting examples of chelators covalently linked to a solid phase. These conjugates are useful for assaying and scanvenging metal ions. The conjugates are as follows:

The class of conjugates, designated CONJ8, each with a chelator covalently linked to a solid phase Z and having the structure:

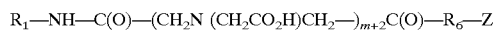

wherein m is 0 or 1. $R_1$ is selected from the group of ring systems consisting of structures (i) to (vi) of FIG. 5. d $R_6$ is selected from the group consisting of: —NH—; —NH—(CH$_2$)$_n$—NHC(S)NH—; and —NH—(CH$_2$)$_n$—NH—C(O)—, wherein n is a number from 1 to 10.

The class of conjugates, designated CONJ9, each with a chelator covalently linked to a solid phase Z and having the structure:

wherein m is 1; $R_1$ is selected from the group consisting of structures (i) and (ii) of FIG. 5.

The class of conjugates, designated CONJ3, each with a chelator covalently linked to a solid phase Z and having the structure:

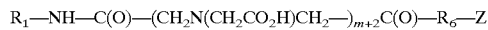

wherein m is 0 or 1. $R_1$ has the structure shown in FIG. 1, wherein (a) in FIG. 1 is any combination of carbon, nitrogen, or sulfur atoms needed to complete a 5-, 6-, or 7-membered aromatic ring. $R_2$ is selected from the group of ring substituents consisting of: —CO$_2$H; —CH$_2$CO$_2$H; —SH; —CH$_2$SH;

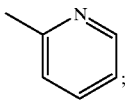

and —C(=N—OR₃)CO₂H, wherein $R_3$ is —CH₃ or —C(CH₃)₂CO₂ᵗBu. $R_6$ is selected from the group consisting of: —NH—; —NH—ø—NHC(S)NH—; —NH—(CH₂)ₙ—NH—C(O)—; —NH—(CH₂)ₙ—NH—C(S)—NH—; —NH—(CH₂)ₙ—NHC(S)NH—ø—NHC(S)NH—, wherein n is a number from 1 to 10.

VII. Immunoassays

The present invention provides assays for detecting or quantifying specific metal ions of interest (i.e., target metal ions) present in a test sample by detecting chelates formed by the test sample. While any assay configuration useful in detecting or measuring preferably low molecular weight haptenic species, can be used to detect or determine the concentration of a chelate of the present invention, competition fluorescence polarization immunoassays (FPIA) are preferred and may be used to illustrate the general procedures and principles underlying such assays:

Generally, FPIA are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution.

When performing FPIA for the quantitation of a given metal ion according to the present invention, a test sample containing the target chelate (obtained by treating the sample with excess chelator) is mixed with the biological binding agent and the fluorescent tracer. Plane polarized light is then passed through the solution and the degree of polarization of the resulting fluorescent emission is monitored as a measure of the amount of target metal ions present in the test sample. Such an assay configuration is illustrated in FIG. 11. Thus, the following presents an example of an FPIA for a metal ion:

The test sample, which may be any aqueous sample containing the target metal ion, is treated with an excess of a chelator of the present invention (in unconjugated form) to convert target metal in the sample into the form of the corresponding chelate. It is understood that, in some cases, test samples will be acidic, as in for example, acid extracts of soil samples or animal tissues. In these cases, subsequent to addition of the chelator, a suitable base is added to bring the pH of the solution into the range of pH 6 to 9. In other cases, aqueous samples may be at or near neutral pH and no pH adjustment is needed. In either case, a buffer or salt may optionally be added together with the chelator, to stabilize the pH in a range that is optimal for antibody binding. After treatment with the chelator, the resulting solution is incubated together with: (a) a biological binding agent specific for the target chelate according to the present invention, and (b) a tracer consisting of the same chelate conjugated to a label, such as a fluorophore in the case of FPIA.

In the case where the assay is used to detect and quantify metal ions in an organism such as a human, the test samples may be biological fluids such as whole blood, serum, plasma, cerebral spinal fluid, or synovial fluid. The assay can also be used for soil samples, sewage and industrial waste and discharge. Furthermore, the assay is useful for quality control of chemicals, solutions and reagents in industrial applications. The assay may be used to monitor the water and reagents involved in manufacturing process streams to ensure that they meet standards of metal contamination or purity. These are non-limiting examples of test samples, other test samples have also been discussed above. Other suitable uses and test samples would be apparent to one skilled in the art based on the discussion herein.

For ease of discussion, the following uses an antibody as a non-limiting example of a biological binding agent. The concentration of the antibody and tracer are selected such that the chelate formed by the target metal ion present in the test sample competes effectively with the tracer for a limited number of antibody binding sites, within the sample metal ion concentration range of interest. Measurement of the fluorescence polarization of the resulting solution provides a measure of the proportion of fluorophore that is bound to antibody. The concentration of target metal ion in the sample is then calculated from a standard curve that relates fluorescence polarization to metal ion concentration.

A preferred fluorescence polarization immunoassay for detecting cadmium (II) ions uses: (1) a polyclonal antibody population which recognizes the chelate comprising a chelator complexed with cadmium (II) ions. The chelator is of CHELATOR4 class, having m is 1, $R_1$ selected from the group consisting of structures (i) and (ii) of FIG. 5, and $R_4$ selected from the group consisting of: —NH—(CH₂)₆—NH₂, and NhnBu; and (2) a conjugate of CONJ7 class.

The FPIA can be conducted using commercially available instruments such as the IMx® and Tdx® analyzers (from Abbott Laboratories, Abbott Park, Ill.), and analyzers from Panvera, Inc., Madison, Wis.

While particularly useful in developing sensitive and specific immunoassays for metal ions, antibodies of the present invention are expected to find use in a wide variety of other applications. For example, antibodies according to the present invention could be immobilized on a solid phase and the resulting affinity matrix used to recover metal ions from process streams (e.g., gold in electroplating, silver in photographic processing, etc.). Numerous such examples will be evident to those skilled in the art. Solid phase materials may include cellulose materials, such as paper and nitrocellulose; natural and synthetic polymeric materials, such as polyacrylamide, polystyrene, and cotton; porous gels such as silica gel, agarose, dextran and gelatin; and inorganic materials such as deactivated alumina, magnesium sulfate and glass. Suitable solid phase materials may be used in assays in a variety of well known physical configurations, including microtiter wells, test tubes, beads, strips, membranes, and microparticles. A preferred solid phase for a non-immunodot assay is a polystyrene microwell, polystyrene beads, or polystyrene microparticles. A preferred solid phase for an immunodot assay is nitrocellulose or nylon membrane.

In addition to FPIA, various other immunoassay formats known in the art can be followed and modified for the detection and/or quantification of a specific metal ion according to the present invention. Such immunoassay system formats include, but are not intended to be limited to, competitive, sandwich and immunometric techniques. Given the teaching in this patent application, one skilled in the art would be able to modify the known assay methods and use them with the chelators, conjugates, and antibodies of the present invention to detect and/or quantify target metal ions. Non-limiting examples of such assays are described in the references cited in the section, "Background of the Invention", above, such as theh assay for detecting metal ions in a fluid as described in U.S. Pat. No. 4,722,892, of Meares. These references are hereby incorporated by reference in their antirey.

In an example of a direct assay, the chelators are attached to a solid phase and then incubated with a test sample. If metal ions are present in the sample they will form a chelate and become affixed to the solid phase.

After the chelate has formed, unbound materials and reagents are removed by washing the solid phase and the immobilized chelate is reacted with a solution containing labelled antibodies directed against it. For example, the labelled antibody can be horseradish peroxidase-labeled goat antibody. This peroxidase labelled antibody then binds to the chelate already affixed to the solid phase. In a final reaction the horseradish peroxidase is contacted with o-phenylenediamine and hydrogen peroxide which results in a yellow-orange color. The intensity of the color is proportional to the amount of metal ions which initially bind to the chelator affixed to the solid phase. Given the teaching in this patent applicaiton, one skilled in the art would be able to modify assay methods known in the art, such as the method for detecting a metal ions in a fluid described in U.S. Pat. No. 4,722,892 of Meares (hereby incorporated by reference in its entirety), for use with the chelators and antibodies of the present invention.

In an example of a solid phase assay in which an antibody is used to detect a metal ion captured by a solid phase, the antibody recognizes: (a) the chelator of CHELATOR4 class, and (b) a solid phase conjugate of CONJ3 class.

(a) Further Non-Limiting Examples of Immunoassays

Given the teaching in this patent application, one skilled in the art would realize that immunoassays for metal ions can be configured using any of the chelators and label-chelator conjugates provided by the present invention. One skilled in the art will readily recognize that the nature of the particular chelator structure chosen for use in immunization (the "immunizing chelator"), or other forms of biological binding agent production, will determine the subsequent choice of a chelator and a chelator-label conjugate as assay components for use in conjunction with that particular biological binding agent. As a successful assay is based on specific binding of a biological binding agent to a particular chelate structure, the structures of: (i) the chelator in the macromolecular carrier-chelator conjugate, (ii) the chelator in the label-chelator conjugates, and, (iii) the sample treatment chelator that is added to the test solution, should preferably be closely matched, if not identical.

EXAMPLE A

This non-limiting example illustrates what "closely matched" means, by defining a set of immunizing structures, label-chelator conjugates and sample treatment chelators that are sufficiently narrow that workable immunoassays can be reduced to practice using any combination of the following immunizing chelators, label-chelator conjugates, and the sample treatment chelators:

(i) Macromolecular Carrier-chelator Conjugates:

CONJ4, wherein m is 1, $R_1$ is structure (i) of FIG. 5 and X is an immunogenic moiety. $R_6$ is selected from the group consisting of: —NH—, —NH—$(CH_2)_n$—NHC(S)NH—, and —NH—$(CH_2)_n$—NH—C(O)—, wherein n is a number from 1 to 10.

The immunogenic moiety is preferably a protein, polypeptide, peptide, carbohydrate, polysaccharide, lipopolysaccharide, poly(amino) acid, or nucleic acid. More preferably, a conventional immunogenic moiety is used, such as BSA, KLH, thyroglobulin, and IgG.

(ii) Label-chelator Conjugates:

CONJ7, wherein m is 1, $R_1$ is structure (i) of FIG. 5, Y is fluorescein and $R_6$ is selected from the group consisting of: —NH—; and —NH$((CH_2)_6)$NHC(S)NH—.

(iii) Sample Treatment Chelators:

CHELATOR4, wherein m is 1, $R_1$ is structure (i) of FIG. 5 and R4 is $NHR_5$, wherein $R_5$ is selected from the group consisting of: -alkyl having from one carbon to ten carbons; -aryl having from six carbons to twenty carbons; -sulfonated alkyl having from one carbon to ten carbons; and -sulfonated aryl having from six carbons to twenty carbons;

Thus, a non-limiting example of a fluorescence polarization immunoassay method for measuring the concentration of a target metal ion in a test solution would comprise the steps of:

(a) Contacting the test solution with a sample treatment chelator selected from the section, "(iii) sample treatment chelators:", above, such that the target metal ion is complexed by the sample treatment chelator to form a chelate;

(b) Contacting the solution from (a) with:
   an antibody raised against the complex formed between the target metal ion and a macromolecular carrier-chelator conjugate selected from the section, "(i) macromolecular carrier-chelator conjugates:", above. The antibody binds specifically to the chelate present in the complex formed between the target metal ion and the macromolecular carrier-chelator conjugate, and;
   a label-chelator conjugate (selected from the "(ii) label-chelator conjugates:" section, above) complexed with the target metal ion; and (c) Incubating the resulting solution to allow the chelate formed in step (a) and that present in the conjugate added in step (b) to compete for a limited concentration of antibody binding sites, then;

(d) Measuring the polarization of the light emitted by the resulting solution when it is excited with plane polarized light, and;

(e) Determining the concentration of target metal ion present in the test solution from a standard curve that relates polarization to target metal ion concentration.

VIII. Scavenging of Metal Ions

While particularly useful in immunoassays, antibodies of the present invention are expected to find use in a wide variety of other applications. For example, antibodies of the present invention are useful in separating and recovering particular metal ions from mixtures of other metal ions using immunoaffinity techniques. Metal ions can be detected or separated from a solution containing metal ions, e.g., by adding the chelator of the present invention to the solution and passing the solution over a solid phase to which the antibodies of the present invention have been pre-bound. The antibodies thus capture the chelate. Thus, the antibodies are useful for recovering metal ions from process streams (e.g., gold in electroplating, silver in photographic process, etc.). Numerous such examples will be evident to those skilled in the art.

Thus, a non-limiting example of a separation method, for the recovery or removal of target metal ions from a solution, will have the following steps:

(a) contacting the solution with a chelator of CHELA-TOR4 class for a sufficient time for the chelator to complex with one or more of the target metal ions to form a target-chelate;

(b) contacting the resulting solution with a biological binding agent that is immobilized on a solid phase, the biological binding agent specifically binds to the target-chelate. The biological binding agent does not bind to non-target-chelates, such as the same chelator of CHELATOR4 class complexed with non-target metal ions;

(c) separating the solution from the solid phase and removing the material unbound to the solid phase; and (d) eluting the target metal ions from the chelate that is bound to the biological binding agent on the solid phase.

One skilled in the art would realize that in the above example, any chelator of the present invention may be used, so long as the biological binding agent is specific to the corresponding target-chelate (i.e., the chelator used as complexed with the target metal ions).

VIX. Test Kit

A test kit according to the present invention comprises all of the essential reagents required to perform a desired immunoassay for the detection and/or quantification of a specific metal ion in a test sample. A non-limiting example of such a kit is one which includes one or more of the following: sample preparation reagents, wash reagents, detection reagents and signal producing reagents, preferably in separate containers. Examples of such immunoassays include a FPIA. The test kit is preferably presented in a commercially packaged form as a combination of one or more containers holding the necessary reagents, as a composition or admixture where the compatibility of the reagents will allow. It is to be understood that the test kit can, of course, include other materials as are known in the art and which may be desirable from a user standpoint, such as buffers, diluents, standards, and the like.

Particularly preferred is a test kit for the FPIA quantification of a specific metal ion in a test sample, comprising any chelators, tracers, and antibodies as described in this patent application for the quantification of a specific metal ion.

The invention may be better understood with reference to the accompanying examples, which are intended for purposes of illustration only and should not be construed as in any sense as limiting the scope of the invention as defined in the claims appended hereto.

EXAMPLES

In the following examples, the chemicals are identified with numerals within parentheses, according to their designations in FIGS. 6 and 7.

Example 1

Synthesis of diethylenetriamine-N(-(2)-(2-amidomethyl)(α-(1-tert butoxycarbonyl)-1-methylethoxyimino)-4-thiazoleacetic acid)-N,N',N'', N'''-tetraacetic acid monoanhydride [(3) of FIG. 6]

This example presents the synthesis of a particularly preferred chelator in the form of the monoanhydride, which is highly reactive with amines.

(Z)-2-Amino-α-(1-tert-butoxycarbonyl)-1-methylethoxyimino)-4-thiazoleacetic acid (0.66 g, 2.0 mmole (1) of FIG. 6) was dissolved in dimethyl sulfoxide (2.0 mL, 99.9%). Brief heating and physical agitation were required to produce complete dissolution. The resulting straw colored solution was added drop-wise to a stirred solution of the cyclic dianhydride of diethylenetriamine pentaacetic acid (0.72 g, 2.0 mmole (2) of FIG. 6) in DMSO (2.0 mL, 99.9%), obtained by brief heating and stirring. The clear yellow reaction solution that resulted was stirred and heated until the solution began to reflux, causing a color change to pale orange. Heating was stopped immediately and the solution was allowed to cool to room temperature.

Under these conditions, conversion of (2) into (3) was essentially quantitative and the concentrated pale orange solution of (3) obtained above was immediately converted into the desired end product (i.e., an immunogen, tracer, or pre-treatment chelator) without attempting to isolate the reactive intermediate.

Example 2

Preparation of a Protein-Chelator Conjugate (4) by Direct Reaction of (3) with Bovine Serum Albumin (BSA)

This example presents a procedure whereby the chelator of EXAMPLE 1 is coupled to a protein (BSA) to produce an immunogenic, macromolecular form of the chelator.

A 0.5 M stock solution of (3) in DMSO was prepared exactly as described in EXAMPLE 1. An aliquot of this solution (2.0 mL, 1.0 mmole) was added drop-wise to a stirred solution of BSA (5.0 mL of a 6 mg/mL solution in 1.0 M sodium bicarbonate buffer, pH 9). The reaction of (3) with the protein produced considerable foaming but no precipitate and the final pH was between 8 and 9.

The resulting conjugate solution was diluted with buffer (0.1 M iminodiacetic acid/0.05 M citric acid, pH 6, 7.0 mL), to reduce the DMSO content to below levels that damage dialysis tubing, then dialyzed extensively (MW cut-off=10 kD) against multiple changes of 0.1 M iminodiacetic acid/ 0.05 M citric acid, pH 6. Ultraviolet (UV) spectroscopy versus unmodified BSA showed that the resulting conjugate (4), FIG. 6, contained approximately 8 chelating groups per protein molecule.

Example 3

Loading a Protein-Chelator Conjugate (4) with Cadmium (II) to Produce an Immunogen (5)

This example presents a method by which the BSA-chelator conjugate of EXAMPLE 2 is loaded with a metal ion ($Cd^{2+}$) to provide a cadmium chelate-protein immunogen.

An aliquot of a BSA conjugate (4), produced according to EXAMPLE 2 (10 mL, 12.8 mg, in 0.1 M iminodiacetic acid/0.05 M citric acid, pH 6) was stirred and a stock 10 mM solution of cadmium (II) nitrate was added drop-wise (1.0 mL, 10 μmoles Cd). The resulting clear solution was stirred at room temperature for 36 hr then dialyzed extensively against 0.1 M iminoacetic acid/0.05 M citric acid, pH 6 to give the cadmium-loaded immunogen (5) of FIG. 6.

Example 4

Synthesis of diethylenetriamine-N(-(-(2)-(2-amidomethyl)(α-(1-tert butoxycarbonyl)-1-methylethoxyimino)-4-thiazoleacetic acid)-N''-(n-butylamidomethyl)-N, N', N''-triacetic acid (6) of FIG. 6)

This example presents a procedure whereby the chelator of EXAMPLE 1 is reacted with n-butylamine, to give a form of the preferred chelator that is suitable for pre-treatment of metal-containing samples.

An aliquot of (2) (2.85 g, 8.0 mmole) was suspended in DMSO (8 mL, 99.9%) stirred and heated to reflux. A solution of (1) (2.64 g, 8.0 mmole) in DMSO (8 mL, 99.9%) was added drop-wise to the refluxing solution, followed immediately by drop-wise addition of a solution of n-butylamine (0.59 g, 8.0 mmole) in DMSO (2 mL, 99.9%). Heating was stopped and the clear orange-red reaction solution was allowed to cool to room temperature, the solution was then added drop-wise to a stirred solution of concentrated HCl (1.0 mL) in deionized water (600 mL), producing an immediate floculent white precipitate. This was filtered off, washed with 0.1 M HCl (2×10 mL) and dried under vaccum to give the product (6) of FIG. 6 as a white amorphous solid. Yield=2.22 g (37%).

Example 5

Synthesis of a Fluorescein-Chelator Conjugate (9) Directly from (3)

This example presents a procedure whereby the chelator of EXAMPLE 1 is reacted with fluoresceinamine to produce a chelator-fluorophore conjugate.

A 0.5 M stock solution of (3) in DMSO was prepared as described in EXAMPLE 1. An aliquot of this solution (1.0 mL, 0.5 mmole) was added drop-wise to a stirred solution of fluoresceinamine (isomer I) [(8)](0.18 g, 0.5 mmole) in DMSO (1.0 mL, 99.9%). The resulting solution was stirred and heated until it began to reflux, then the heat was removed and the clear, red-brown reaction solution was allowed to cool to room temperature. Subsequent drop-wise addition to stirred deionized water gave the product (9) in the form of a brick red precipitate, which could be filtered off and dried under vacuum to provide a solid form of the metal-free fluorescein-chelator tracer for long term storage. However, as mechanical losses and adventitious metal contamination can be problematic when working with the solid tracer, it was generally more convenient to store the metal free tracer in the form of an aqueous 10 mM stock solution, obtained as in the following example.

Example 6

Preparation and Cadmium Loading of an Aqueous Tracer Stock

This example presents a procedure whereby the chelator-fluorophore conjugate of EXAMPLE 5 is converted to the cadmium (II) chelate, which comprises a fluorescent tracer molecule useful in immunoassays.

A 0.25 M DMSO stock solution of (9) was prepared as described in EXAMPLE 5. A 0.4 mL aliquot of this solution (0.1 mmole) was added drop-wise to stirred, deionized water (9.6 mL), producing a dense brick red precipitate. Stirring was continued and 1 M aqueous NaOH was added drop-wise until all of the precipitate re-dissolved to give a clear, pale yellow solution, pH 10. The resulting 10 mM aqueous metal-free tracer stock (9) was divided into 1.0 mL aliquots. Unused aliquots were stored, protected from light, at −20° C.

To produce the cadmium-loaded tracer (10), a 1.0 mL aliquot of the 10 mM free tracer stock (10 µmoles) was pipetted into a tube and stirred as concentrated HCl (0.2 mL) was added, giving a straw colored solution. A 20 mM stock solution of aqueous Cd(NO$_3$)$_2$ (0.5 mL, 10 µmoles) was added to the stirred contents of the tube, followed by 1 M aqueous NaOH to pH 10. The resulting clear yellow solution was transferred to a volumetric flask and diluted with deionized water to a final volume of 100 mL. This stock solution of 0.1 mM cadmium-loaded tracer (10) was divided into aliquots and stored at −20° C. and protected from light until needed.

Example 7

Use of the Cadmium Chelate-BSA Immunogen (5) to Generate Rabbit Polyclonal Antibodies This example presents a procedure whereby the cadmium chelate-BSA immunogen of EXAMPLE 3 is used to generate polyclonal anti-chelate antibodies in rabbits.

The immunogen (5) from EXAMPLE 3 (1 mg/mL in 0.1 M iminodiacetic acid/0.05 M citric acid, pH 6) was emulsified with Freund's adjuvant (complete adjuvant for the primary immunization, incomplete adjuvant for booster doses) and administered to female New Zealand white rabbits (4–6 months old) via multiple subcutaneous injections along each flank. The primary dose contained 1 mg of immunogen, while booster doses contained 0.1 mg of the same preparation. The animals were bled periodically via a peripheral ear vein and the serum tested for the presence of antibodies by titering serial dilutions against a fixed concentration of tracer (10), as described in the next EXAMPLE. A specific response was characterized by a highly polarized fluorescent signal that could be reduced to levels typical of unbound tracer by addition of excess non-fluorescent analog (7), which forms the basis of the immunoassay.

Example 8

Fluorescence Polarization Immunoassay (FPIA) for Cadmium Chelate Standards (7) in Water This example presents a fluorescence polarization immunoassay (FPIA) wherein the tracer molecule of EXAMPLE 6 and differing concentrations of the cadmium complex of the chelator of EXAMPLE 4 compete for a limited number of binding sites provided by an antibody of EXAMPLE 7.

1.0 mL of a 10 mM stock solution of chelator (6), obtained by dissolving solid (6) in deionized water and adding aqueous 1 M aqueous NaOH to pH 8, was pipetted into a tube. The solution was stirred and concentrated HCl (0.2 mL) was added, giving a cloudy, straw-colored solution. Stirring was continued as 0.5 mL of a 20 mM aqueous stock solution of Cd(NO$_3$)$_2$ was added drop-wise, followed by 1 M aqueous NaOH to pH 10. The resulting clear, straw-colored solution was transferred to a volumetric flask and diluted to 100 mL to give a 100 µM stock solution of the 1:1 cadmium-chelate (7).

Further dilution of this 100 µM stock into PBSA (0.01M sodium phosphate buffered saline, pH 7.4, containing 0.1% sodium azide) gave a set of standards containing 0, 5, 10, 50, 100, 500 and 1000 nM (7) respectively. To generate an immunoassay standard curve, a 2.0 mL aliquot of each standard was pipetted into a disposable borosilicate test tube followed by 10 µL of a 0.5 µM stock solution of tracer (10), obtained by dilution of the 100 µM aqueous tracer stock from EXAMPLE 6 into PBSA. Rabbit antiserum, diluted into PBSA, was then added in a fixed amount that had previously been determined to be optimal for the particular antiserum and assay conditions, by titering serial dilutions of antiserum against the same concentration of tracer (10) used in the assay (2.5 nM in this EXAMPLE). In all cases, the total volume of added reagents (tracer and antibody) was ≦100 μL, so that sample dilution resulting from these additions was held to ≦5%. After incubation at room temperature for 15 minute, each tube was transferred to a fluorescence polarization analyzer (FPM-1™, Jolley Consulting & Research, Inc., Grayslake, Ill.) and the fluorescence polarization of the sample was measured. FIG. 8 shows the resulting data plotted as a standard curve that relates the concentration of cadmium chelate (7) to the blank-subtracted fluorescence polarization of the sample, expressed in milli-polarization units (mP). The blank value [10 μL of 0.5 μM tracer (10) in 2.0 mL PBSA with no antiserum present] was 39 mP.

Binding of tracer to the antibody remained strongly inhibited at cadmium chelate concentrations down to 100 nM, the dynamic range of the assay being 0–100 nM. As anticipated for a homogeneous competitive inhibition assay, the greatest signal change, and hence greatest sensitivity was seen at the lowest analyte concentrations. The limit of detection of the assay (LOD) in this configuration was determined in a separate study in which replicates of five 0 nM standards and five 1.0 nM standards were prepared and analyzed exactly as described above, with the following results:

|  | Fluorescence Polarization (mP)* | |
| --- | --- | --- |
| Replicate | 0 nM | 1.0 nM |
| 1 | 191.0 | 182.1 |
| 2 | 193.5 | 183.4 |
| 3 | 194.0 | 185.7 |
| 4 | 193.3 | 185.3 |
| 5 | 191.4 | 184.8 |
| Mean | 192.6 | 184.3 |
| SD | 1.2 | 1.3 |

*Each value is the mean of duplicate readings.

Based on the conventional definition of LOD as 2 standard deviations above zero, the LOD of the present assay for cadmium in the form of its chelate (7) is below 1.0 nM (50 ppt).

Example 9

FPIA for Cadmium Chelate Standards (7) in the Presence of Excess Free Chelator (6)

This example presents evidence that the polyclonal antibodies of EXAMPLE 7 show low cross-reactivity with the metal-free chelator. An FPIA analogous to that of EXAMPLE 8 is performed, except that a fixed excess of the metal-free chelator of EXAMPLE 4 is present in each of the cadmium chelate standards.

The data in EXAMPLE 8 establish that polyclonal antibodies raised against a chelate of the present invention can be used to configure a sensitive immunoassay for cadmium in the form of its chelate (7). However, in order to be useful, such an immunoassay must be sensitive and specific. Two forms of specificity are important in the present context. The first is specificity for the target chelate relative to the free chelator; the second is specificity relative to other, non-target metal complexes of the same chelator. The latter is dealt with in EXAMPLE 10, the former is the subject of this example:

To evaluate the ability of polyclonal antibodies raised against cadmium chelates of the present invention to bind to the target complex (7) in the face of excess free chelator (6), the following assay was performed. A set of cadmium chelate standards containing 0, 5, 10, 25, 50, and 100 nM concentrations of (7) in PBSA were prepared as described in EXAMPLE 8. A 2.0 mL aliquot of each standard was then processed by the same procedure given in EXAMPLE 8 except that, prior to the addition of tracer and antibody, 5 μL of a 100 μM stock of free chelator (6) (obtained as described in EXAMPLE 8) was added to each tube, producing a final fixed free chelator concentration of 250 nM (6). The fluorescence polarization of each standard was measured as described in EXAMPLE 8 and the resulting data are shown in FIG. 9. Under these conditions, if cross-reactivity of the antiserum with free (6) was high, strong inhibition of tracer binding (and therefore a depolarized signal) would be expected at all cadmium concentrations. The observed ability to generate a standard curve therefore demonstrates that chelators of the present invention can be used to produce chelate-specific polyclonal antibody populations that show low cross-reactivity with the free chelator.

Example 10

FPIA for Cadmium Chelate Standards (7) in the Presence of Excess Non-target Chelate This example presents evidence that the polyclonal antibodies of EXAMPLE 7 show low cross-reactivity with non-target chelates. An FPIA analogous to that in EXAMPLE 8 is performed, except that a fixed excess of a non-target metal complex (Cu, Zn, or Hg) of the chelator of EXAMPLE 4 is present in each cadmium chelate standard.

The second type of specificity important in an anti-chelate antibody, i.e., specificity for the chelate of the target metal relative to those of non-target metal ions was evaluated using a procedure analogous to that in EXAMPLE 9. Again, a set of cadmium chelate standards containing 0, 2.5, 5, 10, 25, 50, and 100 nM concentrations of (7) in PBSA were prepared, starting from a 10 mM stock solution of (6), as described in EXAMPLE 8. The same 10 mM stock solution of (6) was also used to prepare 100 μM stock solutions of the analogous chelates with Cu(II), Zn(II), and Hg(II), following the same procedure described in EXAMPLE 8. An assay was then performed in which 2.0 mL aliquots of each cadmium chelate standard were processed exactly as described in EXAMPLE 8, except that, prior to the addition of tracer and antibody, 5 μL of either the 100 μM copper, zinc, or mercury chelate stock was added to each tube, producing a final concentration of 250 nM non-target chelate. The resulting standard curves are shown in FIG. 10. In the case of each of the three non-target metal ions, it was possible to generate a standard curve, i.e., to observe specific displacement of (10) by (7) in the presence of excess non-target analog of (7). This is only possible when cross-reactivity of the limited number of antibody binding sites in the assay with the non-target chelate is low. These results thus confirm the ability of chelators of the present invention to produce polyclonal antibody populations that selectively bind a target chelate.

Example 11

Preparation of a Tracer from an Amine-Functionalized Chelator and an Amine-Reactive Fluorophore This example presents the synthesis [which includes cadmium (II) loading and evaluation] of an alternative tracer, compound (H) (FIG. 2), wherein P is fluorescein, m is 1, n is 6, and $R_1$ is the structure (i) of FIG. 5, wherein $R_3$ is —$C(CH_3)_2CO_2{}^tBu$.

A 0.25 mM stock solution of (3) in DMSO was prepared as described in EXAMPLE 1. A 4.0 mL aliquot of this solution was then stirred as a solution of 1, 6-diaminohexane (0.12 g, 1.0 mmole) in DMSO (1.0 mL, 99.9%) was added drop-wise. The resulting solution, which contained (B), FIG. 2, was stirred and heated to reflux, then fluorescein isothiocyanate (0.38 g, 1.0 mmole) in DMSO (5.0 mL, 99.9%) was added drop-wise. Heating was discontinued and the clear red-orange reaction solution was allowed to cool to room temperature.

A 1.0 mL aliquot of the reaction solution was added drop-wise to 9.0 mL stirred deionized water, producing a dense yellow precipitate. Stirring was continued and 1 M aqueous NaOH was added, until the precipitate dissolved to give a 10 mM aqueous conjugate stock, pH 11. A 1.0 mL aliquot of this 10 mM conjugate stock [(H) of FIG. 2] was converted to the cadmium chelate, using the procedure of EXAMPLE 6, to provide the cadmium loaded tracer. When the latter tracer was used in place of tracer (10) in the assay described in EXAMPLE 8, comparable results were obtained. Thus, in this instance, either reaction sequence (that of EXAMPLE 5 or that of this example) leads to tracer molecules that are useful in immunoassays.

All publications and patent applications mentioned in this patent application are herein incorporated by reference to the same extent as if each of them had been individually indicated to be incorporated by reference.

Although the foregoing invention has been described in some detail by way of illustration and example for purposes of clarity and understanding, it will be obvious that various modifications and changes which are within the skill of those skilled in the art are considered to fall within the scope of the appended claims. Future technological advancements which allows for obvious changes in the basic invention herein are also within the claims. Various modifications of the invention in addition to those shown and described herein which are apparent to those skilled in the art from the preceding description are considered to fall within the scope of the appended claims.

I claim:

1. A chelator having the structure selected from the group consisting of:

(a) a chelator, designated CHELATOR1, having the structure (A) of FIG. 1, which is

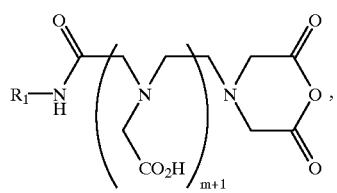

wherein:
m is 0 or 1;
$R_1$ has the structure shown in FIG. 1, which is

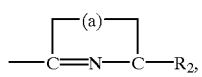

wherein (a) is any combination of carbon, nitrogen, or sulfur atoms needed to complete a 5-, 6-, or 7-membered aromatic ring and $R_2$ is selected from the group of ring substituents consisting of:
—$CO_2H$;
—$CH_2CO_2H$;
—SH;
—$CH_2SH$;

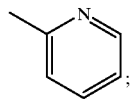

and
—C(=N—$OR_3$)$CO_2H$, wherein $R_3$ is —$CH_3$ or —$C(CH_3)_2{}^tBu$.

(b) a chelator, designated CHELATOR2, having the structure (A) of FIG. 1 wherein m is 0 or 1, and $R_1$ is selected from the group of ring systems consisting of structures (i) to (vi) of FIG. 5 which are the following, respectively:

structure (i) is

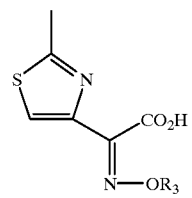

wherein $R_3$ is selected from the group consisting of —$CH_3$ and —$C(CH_3)_2{}^tBu$; structure (ii) is

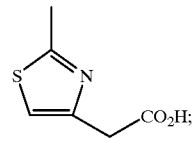

structure (iii) is

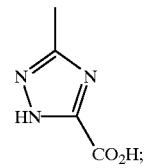

structure (iv) is

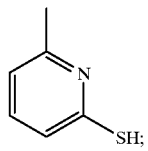

structure (v) is

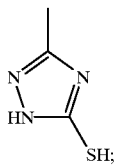

and structure (vi) is

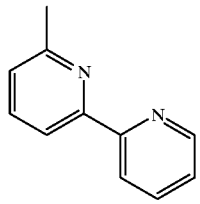

(c) a chelator, designated CHELATOR3, having the structure (A) of FIG. 1 wherein m is 1 and $R_1$ is selected from the group consisting of structures (i) and (ii) of FIG. 5

(d) a chelator, designated CHELATOR4, having the structure shown below:

wherein $R_1$ has the structure shown in FIG. 1, wherein (a) in $R_1$ of FIG. 1 is any combination of carbon, nitrogen, or sulfur atoms needed to complete a 5-, 6-, or 7-membered aromatic ring and $R_2$ is selected from the group of ring substituents consisting of:
—$CO_2H$;
—$CH_2CO_2H$;
—SH;
—$CH_2SH$;

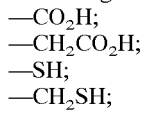

and
—$C(=N-OR_3)CO_2H$, wherein $R_3$ is —$CH_3$ or —$C(CH_3)_2CO_2{}^tBu$;
m is 0 or 1;
$R_4$ is selected from the group consisting of:
—NH—$(CH_2)_n$—$NH_2$, wherein n is a number from 1 to 10;
—NH—Ø—$NH_2$;
—NH—Ø—NCS;
—NH—$(CH_2)_n$—NHC(S)NH—Ø—NCS, wherein n is a number from 1 to 10; and
—$NHR_5$, wherein $R_5$ is selected from the group consisting of: -alkyl having from one carbon to ten carbons; -aryl having from six carbons to twenty carbons; -sulfonated alkyl having from one carbon to ten carbons; and -sulfonated aryl having from six carbons to twenty carbons; and (e) a chelator, designated CHELATOR5, having the structure, represented by formula (E), below:

$R_1$—NH—C(O)—($CH_2N(CH_2CO_2H)CH_2$—$)_{m+2}$COOH   (E)

wherein m is 0 or 1; and
$R_1$ has the structure shown in FIG. 1, wherein (a) is any combination of carbon, nitrogen, or sulfur atoms needed to complete a 5-, 6-, or 7-membered aromatic ring and $R_2$ is selected from the group of ring substituents consisting of:
—$CO_2H$;
—$CH_2CO_2H$;
—SH;
—$CH_2SH$;

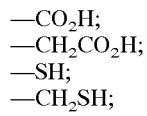

and
—$C(=N-OR_3)CO_2H$, wherein $R_3$ is —$CH_3$ or —$C(CH_3)_2CO_2{}^tBu$.

2. The chelator of claim 1, wherein the chelator is CHELATOR4 selected from the group consisting of:
(a) CHELATOR4, wherein $R_1$ is selected from the group consisting of structures (i) to (vi) of FIG. 5, and $R_4$ is selected from the group consisting of:
—NH—$(CH_2)_n$—$NH_2$, wherein n is a number from 1 to 10;
—NH—Ø—$NH_2$; and
—$NHR_5$ wherein $R_5$ is selected from the group consisting of: -alkyl having from one carbon to ten carbons; and -aryl having from six carbons to twenty carbons; and (b) CHELATOR4, wherein m is 1, $R_1$ selected from the group consisting of structures (i) and (ii) of FIG. 5, and $R_4$ is selected from the group consisting of: —NH—$(CH_2)_6$—$NH_2$, and $NH^nBu$.

3. The chelator of claim 1, wherein the chelator is further complexed with one or more metal ions.

4. The chelator of claim 2, wherein the chelator is further complexed with one or more metal ions.

5. A conjugate comprising a chelator conjugated to a moiety selected from the group consisting of: macromolecular carriers, labels and solid phases, wherein said chelator is selected from the group consisting of: the chelator of claim 1 and the chelator of claim 2.

6. The conjugate of claim 5, wherein the conjugate is selected from the group consisting of:
(a) a conjugate, designated CONJ1, comprising a chelator covalently linked to a macromolecular carrier and having the structure:

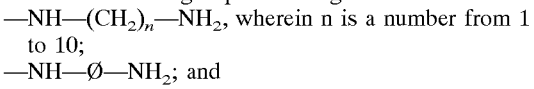

wherein X is the macromolecular carrier; m is 0 or 1;
$R_1$ has the structure shown in FIG. 1, which is

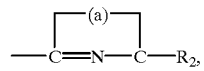

wherein (a) in $R_1$ of FIG. 1 is any combination of carbon, nitrogen, or sulfur atoms needed to complete a 5-, 6-, or 7-membered aromatic ring and $R_2$ is selected from the group of ring substituents consisting of:
—$CO_2H$;
—$CH_2CO_2H$;

—SH;
—CH$_2$SH;

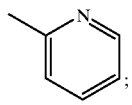;

and
—C(=N—OR$_3$)CO$_2$H, wherein R$_3$ is —CH$_3$ or —C(CH$_3$)$_2$'Bu;
and R$_6$ is selected from the group consisting of:
—NH—;
—NH—Ø—NHC(S)NH—;
—NH—(CH$_2$)$_n$—NH—C(O)—;
—NH—(CH$_2$)$_n$—NH—C(S)—NH—;
—NH—(CH$_2$)$_n$—NHC(S)NH—Ø—NHC(S)NH—;
wherein n is a number from 1 to 10;
(b) a conjugate, designated CONJ2, comprising a chelator covalently linked to a label and having the structure:

wherein Y is the label, m is 0 or 1; R$_1$ has the structure shown in R$_1$ of FIG. 1, wherein (a) in FIG. 1 is any combination of carbon, nitrogen, or sulfur atoms needed to complete a 5-, 6-, or 7-membered aromatic ring and R$_2$ is selected from the group of ring substituents consisting of:
—CO$_2$H;
—CH$_2$CO$_2$H;
—SH;
—CH$_2$SH;
—o—C$_6$H$_4$N; and
—C(=N—OR$_3$)CO$_2$H, wherein R$_3$ is —CH$_3$ or —C(CH$_3$)$_2$'Bu;
and R$_6$ is selected from the group consisting of:
—NH—;
—NH—Ø—NHC(S)NH—;
—NH—(CH$_2$)$_n$—NH—C(O)—;
—NH—(CH$_2$)$_n$—NH—C(S)—NH—;
—NH—(CH$_2$)$_n$—NHC(S)NH—Ø—NHC(S)NH—;
wherein n is a number from 1 to 10;
(c) a conjugate, designated CONJ3, comprising a chelator covalently linked to a solid phase and having the structure:

wherein Z is the solid phase; m is 0 or 1; R$_1$ has the structure shown in R$_1$ of FIG. 1, wherein (a) in FIG. 1 is any combination of carbon, nitrogen, or sulfur atoms needed to complete a 5-, 6-, or 7-membered aromatic ring and R$_2$ is selected from the group of ring substituents consisting of:
—CO$_2$H;
—CH$_2$CO$_2$H;
—SH;
—CH$_2$SH;

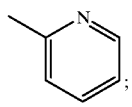;

and
—C(=N—OR$_3$)CO$_2$H, wherein R$_3$ is —CH$_3$ or —C(CH$_3$)$_2$'Bu;

and R$_6$ is selected from the group consisting of:
—NH—;
—NH—Ø—NHC(S)NH—;
—NH—(CH$_2$)$_n$—NH—C(O)—;
—NH—(CH$_2$)$_n$—NH—C(S)—NH—;
—NH—(CH$_2$)$_n$—NHC(S)NH—Ø—NHC(S)NH—;
wherein n is a number from 1 to 10;
(d) a conjugate, designated CONJ4, comprising a chelator covalently linked to a macromolecular carrier and having the structure shown below:

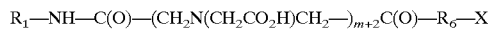

wherein:
X is the macromolecular carrier;
m is 0 or 1;
R$_1$ is as defined is selected from the group of ring systems consisting of structures (i) to (vi) of FIG. 5 which are the following, respectively:
structure (i) is

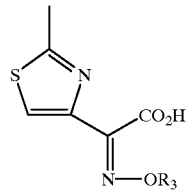

wherein R$_3$ is selected from the group consisting of —CH$_3$ and —C(CH$_3$)$_2$'Bu; structure (ii) is

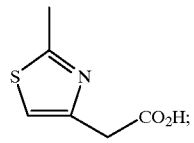

structure (iii) is

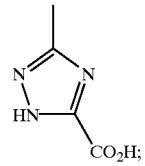

structure (iv) is

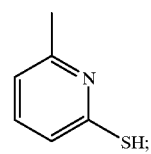

structure (v) is

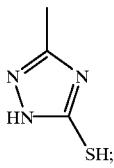

and structure (vi) is

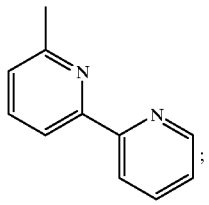

and
R$_6$ is selected from the group consisting of:
—NH—,
—NH—(CH$_2$)$_n$—NHC(S)NH—, and
—NH—(CH$_2$)$_n$—NH—C(O)—, wherein n is a number from 1 to 10;

(e) a conjugate, designated CONJ5, comprising a chelator covalently linked to bovine serum albumin and having the structure shown below:

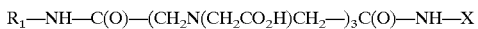

wherein X is the macromolecular carrier, and R$_1$ is selected from the group consisting of structures (i) and (ii) of FIG. 5;

(f) a conjugate, designated CONJ6, comprising a chelator covalently linked to a label and having the structure:

wherein:
Y is the label;
m is 0 or 1;
R$_1$ is selected from the group of ring systems consisting of structures (i) to (vi) of FIG. 5; and
R$_6$ is selected from the group consisting of:
—NH—,
—NH—(CH$_2$)$_n$—NHC(S)NH—, and
—NH—(CH$_2$)$_n$—NH—C(O)—, wherein n is a number from 1 to 10;

(g) a conjugate, designated CONJ7, comprising a chelator covalently linked to a fluorophore and having the structure:

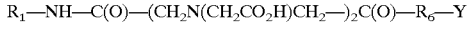

wherein Y is the label;
R$_1$ is selected from the group consisting of structures (i) and (ii) of FIG. 5; and
R$_6$ is selected from the group consisting of:
—NH—; and
—NH—(CH$_2$)$_6$—NHC(S)NH—;

(h) a conjugate, designated CONJ8, comprising a chelator covalently linked to a solid phase and having the structure:

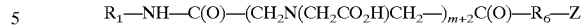

wherein:
Z is the solid phase;
m is 0 or 1;
R$_1$ is selected from the group of ring systems consisting of structures (i) to (vi) of FIG. 5; and
R$_6$ is selected from the group consisting of:
—NH—,
—NH—(CH$_2$)$_n$—NHC(S)NH—, and
—NH—(CH$_2$)$_n$—NH—C(O)—, wherein n is a number from 1 to 10; and (i) a conjugate, designated CONJ9, comprising a chelator covalently linked to a solid phase and having the structure shown below:

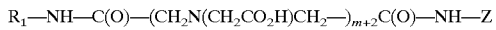

wherein Z is the solid phase; m is 1; R$_1$ is selected from the group consisting of structures (i) and (ii) of FIG. 5.

7. The conjugate of claim 5, wherein:
the labels are selected from the group consisting of: fluorescent compounds, enzymes, radioisotopes, chromophores, chemiluminescent molecules, phosphorescent molecules, and luminescent molecules;
the macromolecular carriers are immunogenic moieties; and
the solid phases are selected from the group consisting of: cellulose materials, natural and synthetic polymeric materials, porous gels, and inorganic materials.

8. The conjugate of claim 5, wherein:
the labels are selected from the group consisting of: fluorescent compounds, enzymes, radioisotopes, chromophores, chemiluminescent molecules, phosphorescent molecules, and luminescent molecules;
the macromolecular carriers are selected from the group consisting of: proteins, polypeptides, peptides, carbohydrates, polysaccharides, lipopolysaccharides, poly(amino acids), and nucleic acids; and
the solid phases are selected from the group consisting of: cellulose materials, natural and synthetic polymeric materials, porous gels, and inorganic materials.

9. The conjugate of claim 8, wherein the macromolecular carriers are: bovine serum albumin (BSA), keyhole limpet hemocyanin (KLH), thyroglobulin, immunoglobulin (IgG).

10. The conjugate of claim 6, wherein:
the label is selected from the group consisting of: fluorescent compounds, enzymes, radioisotopes, chromophores, chemiluminescent molecules, phosphorescent molecules, and luminescent molecules;
the macromolecular carrier is selected from the group consisting of: proteins, polypeptides, peptides, carbohydrates, polysaccharides, lipopolysaccharides, poly(amino acids), and nucleic acids; and
the solid phase is selected from the group consisting of: cellulose materials, natural and synthetic polymeric materials, porous gels, and inorganic materials.

11. The conjugate of claim 10, wherein the conjugate is selected from the group consisting of: CONJ7, wherein the label is a fluorophore; CONJ5, wherein the macromolecular carrier is an immunogenic moiety; and CONJ4 wherein the macromolecular carrier is an immunogenic moiety.

12. The conjugate of claim 8, wherein the conjugate is further completed with one or more metal ions.

13. The conjugate of claim 10, wherein the conjugate is further completed with one or more metal ions.

14. A fluorescence polarization immunoassay method for measuring the concentration of a target metal ion in a test solution, said method comprising the steps of:
 (a) Contacting the test solution with a sample treatment chelator for a sufficient time to allow the target metal ion to complex with the sample treatment chelator to form a chelate;
 (b) Contacting the solution from (a) with:
  (i) an antibody raised against the complex formed between the target metal ion and a macromolecular carrier-chelator conjugate, the antibody binds specifically to the chelate present in the complex formed between the target metal ion and the macromolecular carrier-chelator conjugate, and;
  (ii) a label-chelator conjugate complexed with the target metal ion; and
 (c) Incubating the resulting solution to allow the chelate formed in step (a) and that present in the conjugate added in step (b) to compete for a limited concentration of antibody binding sites, then;
 (d) Measuring the polarization of the light emitted by the resulting solution when it is excited with plane polarized light, and;
 (e) Determining the concentration of target metal ion present in the test solution from a standard curve that relates polarization to target metal ion concentration;
 wherein:
  said macromolecular carrier-chelator conjugate is CONJ4 of claim 6, wherein m is 1, $R_1$ is structure (i) of FIG. 5, which is

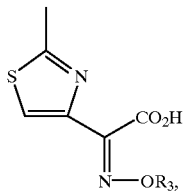

wherein $R_3$ is selected from the group consisting of —$CH_3$ and —$C(CH_3)_2CO_2{}^tBu$, X is an immunogenic moiety, $R_6$ is selected from the group consisting of: —NH—, —NH—$(CH_2)_n$—NHC(S)NH—, and —NH—$(CH_2)_n$—NH—C(O)—, wherein n is a number from 1 to 10;
said label-chelator conjugate is CONJ7 of claim 6, wherein m is 1, $R_1$ is structure (i) of FIG. 5, Y is a fluorescein, and $R_6$ is selected from the group consisting of —NH—, and —NH(($CH_2)_6$)NHC(S)NH—;
said sample treatment chelator is CHELATOR4 of claim 1, wherein m is 1, $R_1$ is structure (i) of FIG. 5 and $R_4$ is $NHR_5$, wherein $R_5$ is selected from the group consisting of: -alkyl having from one carbon to ten carbons; -aryl having from six carbons to twenty carbons; -sulfonated alkyl having from one carbon to ten carbons; and -sulfonated aryl having from six carbons to twenty carbons.

15. The chelator of claim 1, wherein the chelator is CHELATOR4, m is 1, $R_1$ is structure (i) of FIG. 5, which is

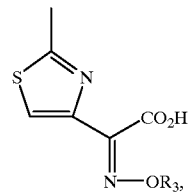

wherein $R_3$ is selected frpm the group consisting of —$CH_3$ and —$C(CH_3)_2CO_2{}^tBu$, $R_4$ is $NHR_5$, wherein $R_5$ is selected from the group consisting of: -alkyl having from one carbon to ten carbons; -aryl having from six carbons to twenty carbons; -sulfonated alkyl having from one carbon to ten carbons; and -sulfonated aryl having from six carbons to twenty carbons.

16. The chelator of claim 1, wherein the chelator is the chelator designated (6) in FIG. 6 which is

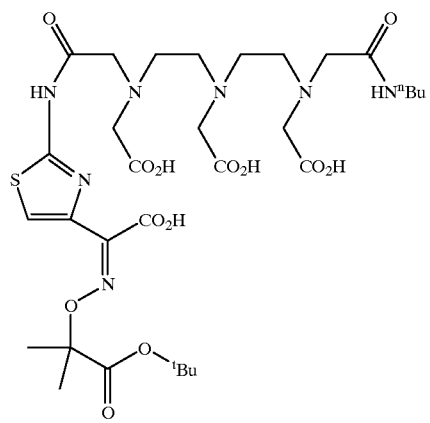

17. The chelator of claim 1, wherein the chelator is CHELATOR4, m is 1, $R_1$ is structure (i) of FIG. 5, which is

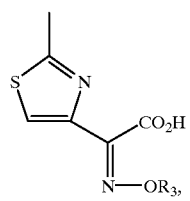

wherein $R_3$ is selected from the group consisting of —$CH_3$ and —$C(CH_3)_2CO_2{}^tBu$, $R_3$ is —$CH_3$, and $R_5$ is a butyl group.

18. The conjugate of claim 6, wherein the conjugate is CONJ4, m is 1, $R_1$ is structure (i) of FIG. 5, which is

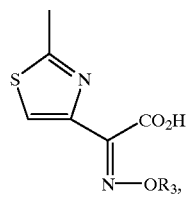

wherein $R_3$ is selected from the group consisting of —$CH_3$ and —$C(CH_3)_2CO_2{}^tBu$, and X is an immunogenic moiety.

19. The conjugate of claim 6, wherein the conjugate is CONJ7, m is 1, $R_1$ is structure (i) of FIG. 5, which is

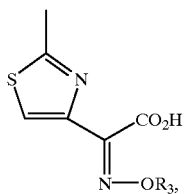
wherein $R_3$ is selected from the group consisting of —$CH_3$ and —$C(CH_3)_2CO_2{}^tBu$, Y is a fluorescein, and $R_6$ is selected from the group consisting of: —NH—; and —NH(($CH_2$)$_6$)NHC(S)NH—.
* * * * *